(12) United States Patent
Baraldi et al.

(10) Patent No.: US 7,094,895 B2
(45) Date of Patent: Aug. 22, 2006

(54) TYROSYL DERIVATIVES AND THEIR USE AS P2X7 RECEPTOR MODULATORS

(75) Inventors: Pier Giovanni Baraldi, Ferrara (IT); Pier A. Borea, Ferrara (IT)

(73) Assignee: King Pharmaceuticals Research & Development, Inc., Cary, NC (US)

( * ) Notice: Subject to any disclaimer, the term of this patent is extended or adjusted under 35 U.S.C. 154(b) by 62 days.

(21) Appl. No.: 10/329,094

(22) Filed: Dec. 23, 2002

(65) Prior Publication Data

US 2003/0181452 A1   Sep. 25, 2003

Related U.S. Application Data

(60) Provisional application No. 60/342,977, filed on Dec. 21, 2001.

(51) Int. Cl.
 *C07D 401/14* (2006.01)
(52) U.S. Cl. ............... 544/295; 544/360; 544/363; 544/364; 544/387; 544/391
(58) Field of Classification Search .......... 514/253.01, 514/253.05, 253.07, 253.12, 255.01; 544/295, 544/360, 363, 364, 387, 391
 See application file for complete search history.

(56) References Cited

U.S. PATENT DOCUMENTS

| 5,081,246 A | 1/1992 | Hidaka et al. ............... 544/363 |
| 5,244,895 A * | 9/1993 | Hidaka et al. ......... 514/253.05 |
| 2003/0232807 A1* | 12/2003 | Poindexter et al. ......... 514/218 |

FOREIGN PATENT DOCUMENTS

EP        513691 A1 * 11/1992

OTHER PUBLICATIONS

Williams, Michael et al, Ann Reports Med. Chem., vol. 31, 1996, pp. 21-30.*

(Continued)

*Primary Examiner*—Thomas C. McKenzie
(74) *Attorney, Agent, or Firm*—Jones Day

(57) ABSTRACT

The present invention relates to compounds of the formula

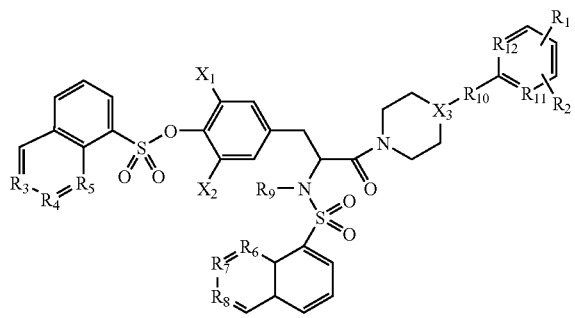

wherein $R_1$ and $R_2$ are independently hydrogen, C1–C4 alkyl, C1–C4 substituted alkyl, C1–C4 alkoxy, C1–C4 substituted alkoxy, C1–C4 acyl, halogen, cyano, nitro, amino, alkylamino, or dialkylamino;
$R_3$, $R_4$, $R_5$, $R_6$, $R_7$, and $R_8$ are independently CH or nitrogen;
$R_9$ is hydrogen or methyl;
$R_{10}$ is C=O or $(CH_2)_n$;
where n is 0, 1, 2, 3, or 4;
$R_{11}$ and $R_{12}$ are independently nitrogen or CH; $X_1$ and $X_2$ are independently hydrogen, deuterium, tritium or halogen; and $X_3$ is N; and their pharmaceutically acceptable salts; compositions thereof. Methods of preparing the compounds are also described. The compounds are useful in the treatment of diseases in mammals that are mediated by the action of the $P2X_7$ receptor.

7 Claims, 4 Drawing Sheets

OTHER PUBLICATIONS

Fisher, Bilha, Exp. Opin. Ther. Patents, 9(4), 1999, pp. 385-399.*
A *copy* of the International Search Report mailed Jun. 6, 2003, issued in corresponding PCT Patent Application No.: PCT/US02/41385.
Gargett et al., 1997, "The Isoquinoline Derivative KN-62 a Potent Antagonist of the P2Z-Receptor of Human Lymphocytes", British Journal of Pharmacology, 120, 1483-1490.
Hidaka et al., 1992, "Pharmacology of Protein Kinase Inhibitors", Annu. Rev. Pharmacolo. Toxicol., 32:377-97.

Kawamura et al., 1996, "Cellular Events Involved in the Sensitization of Etopside-Resistant Cells by Inhibitors of Calcium-Calmodulin-Dependent Processes", Biochemical Pharmacology, vol. 52, pp. 1903-1909.
Maurer et al., 1996, "Effects of Protein Kinase Inhibitors on Morphology and Function of Cultured Bovine Adrenal Chromaffin Cells: KN-62 Inhibits Secretory Function by Blocking Stimulated $Ca^{2+}$ Entry", Journal of Neurochemistry, pp. 105-113.

* cited by examiner

TYROSYL DERIVATIVES AND THEIR USE AS P2X7 RECEPTOR MODULATORS

RELATED APPLICATION

This Application claims the benefit of Provisional Application 60/342,977 filed Dec. 21, 2001.

BACKGROUND OF THE INVENTION

The present invention relates generally to the field of purinergic P2 receptors. More particularly, the present invention relates to novel purinergic P2X receptor compounds and production thereof. In further detail, the present invention relates to compounds, their intermediates, and enantiomers of both which have P2X receptor subtype 7 ($P2X_7$) binding inhibition activity, and are useful for preventing and/or treating diseases associated with adenosine 5'-triphosphate or other natural or synthetic nucleotides.

P2 receptors have been generally categorized as either metabotropic nucleotide receptors or inotropic receptors for extracellular nucleotides. Metabotropic nucleotide receptors (usually designated P2Y or $P2Y_n$, where "n" is a subscript integer indicating subtype) are believed to differ from inotropic receptors (usually designated P2X or $P2X_n$) in that they are based on a different fundamental means of transmembrane signal transduction: P2Y receptors operate through a G protein-coupled system, while P2X receptors are ligand-gated ion channels. The ligand for these P2X receptors is ATP, and/or other natural nucleotides, for example, ADP, UTP, UDP, and/or synthetic nucleotides, for example 2-methylthioATP.

A therapeutic role for P2 receptors has been suggested, for example, for cystic fibrosis (Boucher et al. (1995) in: Belardinelli et al. (eds) Adenosine and Adenine Nucleotides: From Molecular Biology to Integrative Physiology (Kluwer Acad., Norwell Mass.) pp 525–532), diabetes (Loubatieres-Mariani et al. (1995) in: Belardinelli et al. (eds), supra, pp 337–345), immune and inflammatory diseases (Di Virgilio et al. (1995) in: Belardinelli et al. (eds), supra, pp 329–335), cancer (Rapaport (1993) Drug Dev. Res. 28:428–431), constipation and diarrhea (Milner et al. (1994) in: Kamm et al. (eds.) Constipation and Related Disorders: Pathophysiology and Management in Adults and Children (Wrightson Biomedical, Bristol) pp 41–49), behavioral disorders such as epilepsy, depression and aging-associated degenerative diseases (Williams (1993) Drug. Dev. Res. 28:438–444), contraception and sterility (Foresta et al. (1992) J. Biol. Chem. 257:19443–19447), and wound healing (Wang et al. (1990) Biochim. Biophys. Res. Commun. 166:251–258).

At least seven P2X receptors, and the cDNA sequences encoding them, have been identified to date. $P2X_1$ cDNA was cloned from the smooth muscle of the rat vas deferens (Valera et al (1994) Nature 371:516–519) and $P2X_2$ cDNA was cloned from PC12 cells (Brake et al. (1994) Nature 371:519–523). Five other P2X receptors have been found in cDNA libraries by virtue of their sequence similarity to $P2X_1$ and $P2X_2$ ($P2X_3$: Lewis et al. (1995) Nature 377: 432–435, Chen et al. (1995) Nature 377:428–431; $P2X_4$: Buell et al. (1996) EMBO J. 15:55–62, Seguela et al. (1996) J. Neurosci. 16:448–455, Bo et al. (1995) FEBS Lett. 375:129–133, Soto et al. (1996) Proc. Natl. Acad. Sci. USA 93:3684–3688, Wang et al. (1996) Biochem. Biophys. Res. Commun. 220:196–202; $P2X_5$: Collo et al. (1996) J. Neurosci. 16:2495–2507, Garcia-Guzman et al. (1996) FEBS Lett. 388:123–127; $P2X_6$: Collo et al. (1996), supra, Soto et al. (1996) Biochem. Biophys. Res. Commun. 223:456–460; $P2X_7$: Surprenant et al. (1996) Science 272:735–738). For a comparison of the amino acid sequences of rat P2X receptors see Buell et al. (1996) Eur. J. Neurosci. 8:2221–2228.

Native P2X receptors form rapidly activated, nonselective cationic channels that are activated by ATP. Rat $P2X_1$ and rat $P2X_2$ have equal permeability to $Na^+$ and $K^+$ but significantly less to $Cs^+$. The channels formed by the P2X receptors generally have high $Ca^{2+}$ permeability. The cloned rat $P2X_1$, $P2X_2$ and $P2X_4$ receptors exhibit the same permeability for $Ca^{2+}$ observed with native receptors. However, the mechanism by which P2X receptors form an ionic pore or bind ATP is not known.

A variety of tissues and cell types, including epithelial, immune, muscle and neuronal, express at least one form of P2X receptor. The widespread distribution of $P2X_4$ receptors in the rat central nervous system suggests a role for $P2X_4$-mediated events in the central nervous system. However, study of the role of individual P2X receptors is hampered by the lack of receptor subtype-specific agonists and antagonists. For example, one agonist useful for studying ATP-gated channels is α,β methylene ATP (meATP). However, the P2X receptors display differential sensitivity to the agonist with $P2X_1$ and $P2X_2$ being meATP-sensitive and insensitive, respectively. Furthermore, binding of meATP to P2X receptors does not always result in channel opening. The predominant forms of P2X receptors in the rat brain, $P2X_4$ and $P2X_6$ receptors, cannot be blocked by suramin or PPADS. These two forms of the P2X receptor are also not activated by meATP and are, thus, intractable to study with currently available pharmacological tools.

The functional properties of the $P2X_{1-6}$ receptors are fundamentally similar to those of the other two ionotropic receptors, the nicotinic and excitatory amino acid receptors, and are then relatively impermeable to cations that are more than about 200 D.

One of the most interesting members of the ionotropic P2X family is the $P2X_7$ receptor. Di Virgilio, F., et. al. (1998) Cell Death and Differentiation 5:191; Di Virgilio, F., et. al. (1995) Immunology Today 16:524. The $P2X_7$ ionic channel differs strikingly from these channels and it is formed by the aggregation of an unknown number of subunits each 595 aminoacids (AA) long (200 AA longer than the other six P2X receptor), and upon stimulation by high concentrations of extracellular ATP generates a nonselective membrane pore of variable size (3–5 nm) and permeable to hydrophilic molecules with molecular weight up to 900 Dalton. Suprenant, A., et. al. (1996) Science 272:735.

Selective activation of the $P2X_7$ receptor in mycobacterial-infected cells may provide a new therapy for tuberculosis, as well as an effective anticancer agent for many tumors that are rich in $P2X_7$ receptor. This receptor is mainly, if not exclusively, expressed by mononuclear phagocytes, where it mediates cytotoxic responses, cytokine release and cell fusion. Di Virgilio, F., et. al., (1998) Drug Dev. Res. 45:207; Falzoni, S., et. al. (1995) J. Clin. Invest. 95:1207. Activation of the $P2X_7$ receptor in macrophages and microglial cells causes a large and rapid release of mature interleukin-1β in response to lipopolysaccharide (LPS) stimulation.

IL-1β is of prime importance in the induction of the immune responses, including facilitating response to antigens, synthesis of prostaglandins, proliferation of fibroblasts, blood neutrophils, and inducing the synthesis of other cytokines. Due to likely involvement in immunomodulation and in the inflammatory reaction, it would be of the most importance to develop selective $P2X_7$ antagonists.

Human macrophages have proven very useful for the evaluation of $P2X_7$ agonists and antagonists. Compound KN62 (1-N,0-(bis(1,5-isoquinolinesulfonyl)-N-methyl-L-tyrosyl)-4-phenylpiperazine) is one of the most potent antagonists for the $P2X_7$ receptor with complete inhibition at the concentration of 500 nM. Gargett, C. E. et. al. (1997) B. J. Pharmacol. 120:1483. KN62 is a specific cell-permeable inhibitor of the autophosphorylation of $Ca^{2+}$/calmodulin-dependent protein kinase II (CaMK II) and may be useful as a pharmacological tool for evaluating the role of CaMK II. Hidaka, H. et. al. (1992) Ann. Rev. Pharmacol. Toxicol., 32:377 (1992).

CaMK II is one of the important kinases whose response seems to be mediated by calmodulin, and that is proposed as a regulator for the synthesis and vescicular release of neurotransmitters. The same compound KN62 significantly inhibited both stimulated catecholamine release and secretory function via the direct blockade of activated $Ca^{2+}$ influx. Maurer, J. A. et. al. (1996) J. Neurochem 66:105. KN62, at non-cytotoxic concentration (2 μM), enhanced etoposide (VP-16) cytotoxicity in Adriamycin-resistant cells (HL-60) and this is due to enhancement (from 2- to 4-fold) of VP-16 induced topoisomerase II-mediated DNA cleavable complex formation. Kawamura, K., et. al. (1996) Biochem Pharmacol. 12:1903. The DNA damage induced by VP-16 in the presence of KN62 resulted in the rapid introduction of apoptosis and depletion of cell in "S phase" of the cell cycle.

Thus, what is needed is specific agonists and antagonists for the $P2X_7$ receptor subtype and, in particular, agents that will be effective in vivo, useful in the treatment of patients, as well as methods for identifying the $P2X_7$ receptor-specific agonist and antagonist compounds.

BRIEF SUMMARY OF THE INVENTION

The present invention comprises various novel compounds, their intermediates, their pharmaceutically acceptable salts, methods of treatment of medical conditions and methods for identifying receptors in mammals.

It is an object of the present invention to provide novel compounds, their intermediates, and their pharmaceutically acceptable salts.

It is another object of the invention to provide ligands selective for the $P2X_7$ receptor that have a broader therapeutic index than those currently available.

It is a further object of the invention to provide $P2X_7$ receptor antagonists.

It is a further object to of the invention to provide compounds having activity as anti-inflammatories.

It is yet another object of the invention to provide compounds having activity that enhance endocrine function and hormonal modulation.

It is a further object of the invention to provide compounds useful in modulating or inhibiting the immune response.

It is another object of the invention to provide compounds having activity which will induce apoptosis either when administered singly or in combination with other agents.

Additional objects and advantages of the present invention will be apparent in the following detailed description read in conjunction with the accompanying table, and figures.

BRIEF DESCRIPTION OF THE DRAWINGS

Table 1 illustrates the IC50 values for compounds toward inhibiting calcium influx in human monocytes in the presence of 1 mM ATP.

DETAILED DESCRIPTION OF THE INVENTION

The inventors have synthesized and evaluated the antagonist activities of a series of $P2X_7$ receptor ligands.

The general structure of the compounds of the present invention are illustrated in Formulas I, II, III, and IV:

Formula I wherein $R_1$ and $R_2$ are independently hydrogen, C1–C4 alkyl, C1–C4 alkoxy, halogen, cyano, nitro, amino, or C1–C4 acyl;

$R_3$, $R_4$, $R_5$, $R_6$, $R_7$, and $R_8$ are independently CH or nitrogen;

$R_9$ is independently hydrogen or methyl;

$R_{10}$ is independently carbonyl or $(CH_2)_n$; where n is 0, 1, 2, 3, or 4;

$R_{11}$ is independently nitrogen or CH;

$R_{12}$ is independently nitrogen or CH;

$X_1$ and $X_2$ are independently halogen or tritium; and $X_3$ is N or CH.

Formula II wherein $R_1$ is hydrogen, C1–C4 alkyl, C1–C4 alkoxy, C1–C4 acyl, halogen, cyano, nitro, amino, alkylamino, or dialkylamino; $X_1$ and $X_2$ are independently hydrogen, deuterium, tritium, or halogen.; $R_9$ is methyl or hydrogen.

Formula III wherein $R_1$ and $R_2$ are independently hydrogen, C1–C4 alkyl, C1–C4 alkoxy, C1–C4 acyl, halogen, cyano, nitro, amino, alkylamino or dialkylamino; $R_9$ is hydrogen or methyl; $X_1$ and $X_2$ are independently hydrogen, deuterium, tritium, or halogen; and $X_3$ is independently nitrogen or CH.

Formula IV wherein $R_1$ and $R_2$ are independently hydrogen, C1–C4 alkyl, C1–C4 alkoxy, halogen, cyano, nitro, or amino; $R_3$, $R_4$, $R_5$, $R_6$, $R_7$, and $R_8$ are independently CH or nitrogen;

n is 0, 1, 2, 3, 4; and with the proviso that when n is 0 either $R_1$ or $R_2$ is not hydrogen.

Figure 1:
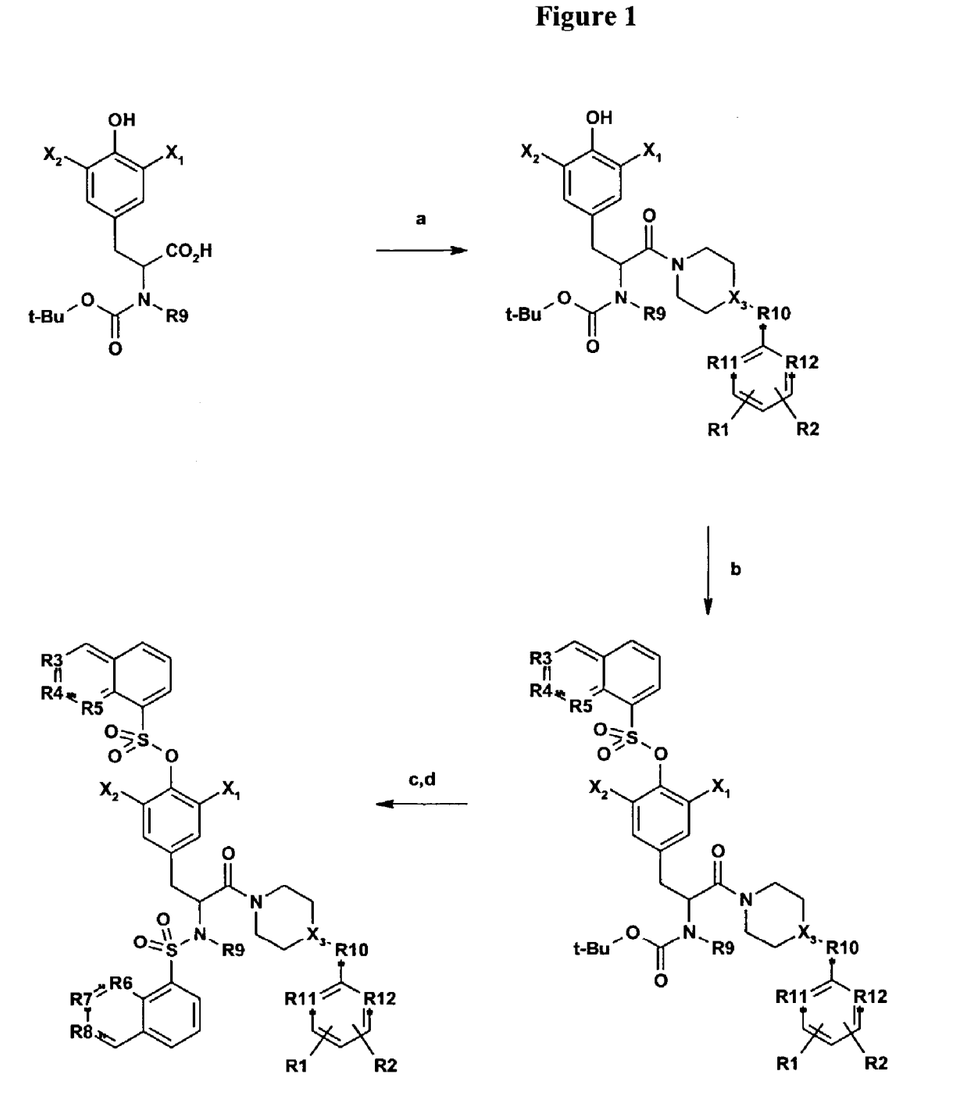
FIG. 1 illustrates the general synthesis procedure for compounds of formula I.

FIG. 1 illustrates the synthetic process for the formation of the compounds of Formula I and their intermediates. In summary, these compounds are prepared from an N-Boc-protected-tyrosine derivative. These amino-protected precursors are converted to the activated 1-hydroxy-1,2,3-benzotriazole (HOBt) esters with HOBt and EDC and coupled with the appropriate substituted-aryl, aralkyl, heteroaryl, or heteroaralkylpiperazines or piperidines to afford the requisite amides in good yields. The phenolic anion of the tyrosyl-moiety compounds (generated in situ with sodium hydride) is converted to the corresponding heteroarylsulfonyl ester by treatment with a dichloromethane ($CH_2Cl_2$) solution of the requisite heteroarylsulfonyl chloride. Removal of the amine protecting tert-butyloxycarbonyl (Boc) group is conveniently effected with trifluoroacetic acid (TFA) in a $CH_2Cl_2$ solution to provide the corresponding free amine. This intermediate is then coupled with an excess of the desired heteroarylsulfonyl chloride to provide the desired sulphonamides in acceptable yields. Reagents and conditions referred to in FIG. 1 are: a. N-substituted aryl, aralkyl, heteroaryl, or heteroaralkyl piperazine or piperidine, HOBt, EDC, DMF. b. Sodium hydride, heteroarylsulfonyl chloride, CH2Cl2. c. Trifluoroacetic acid, CH2Cl2. d. Triethylamine, heteroarylsulfonyl chloride, CH2Cl2.

Figure 2:
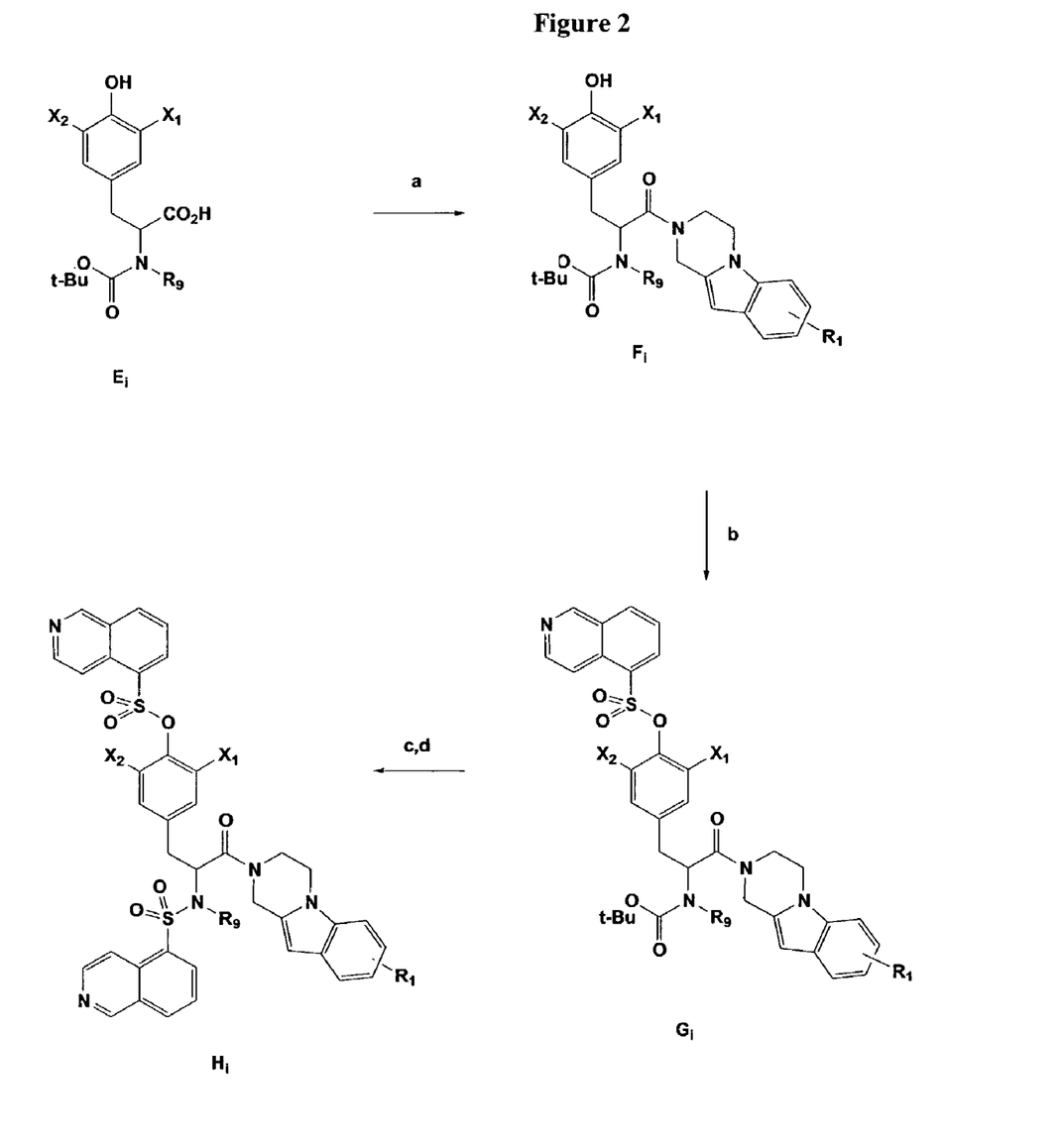
FIG. 2 illustrates the general synthesis procedure for compounds of formula II.

FIG. 2 illustrates the synthetic process for the formation of the compounds of Formula II and their intermediates. In summary, these compounds are prepared from an N-Boc-protected-tyrosine derivative. These amino-protected precursors are converted to the activated 1-hydroxy-1,2,3-benzotriazole (HOBt) esters with HOBt and EDC and coupled with the appropriate 3,4-dihydro-1H-pyrazino[1,2-a]indole to afford the requisite amides in good yields. The phenolic anion of the tyrosyl-moiety compounds (generated in situ with sodium hydride) is converted to the corresponding isoquinolinesulfonyl ester by treatment with a dichloromethane (CH2Cl2) solution of the requisite isoquinolinesulfonyl chloride. Removal of the amine protecting tert-butyloxycarbonyl (Boc) group is conveniently effected with trifluoroacetic acid (TFA) in a CH2Cl2 solution to provide the corresponding free amine. This intermediate is then coupled with an excess of the desired isoquinolinesulfonyl chloride to provide the desired sulphonamides in acceptable yields. Reagents and conditions for the reactions referred to in FIG. 2 are: a. Substituted 1,2,3,4-tetrahydropyrazino[1,2-a]indole, HOBt, EDC, DMF. b. Sodium hydride, isoquinoline-5-sulfonyl chloride, CH2Cl2. c. Trifluoroacetic acid, CH2Cl2. d. Triethylamine, isoquinoline-5-sulfonyl chloride, CH2Cl2.

Figure 3:
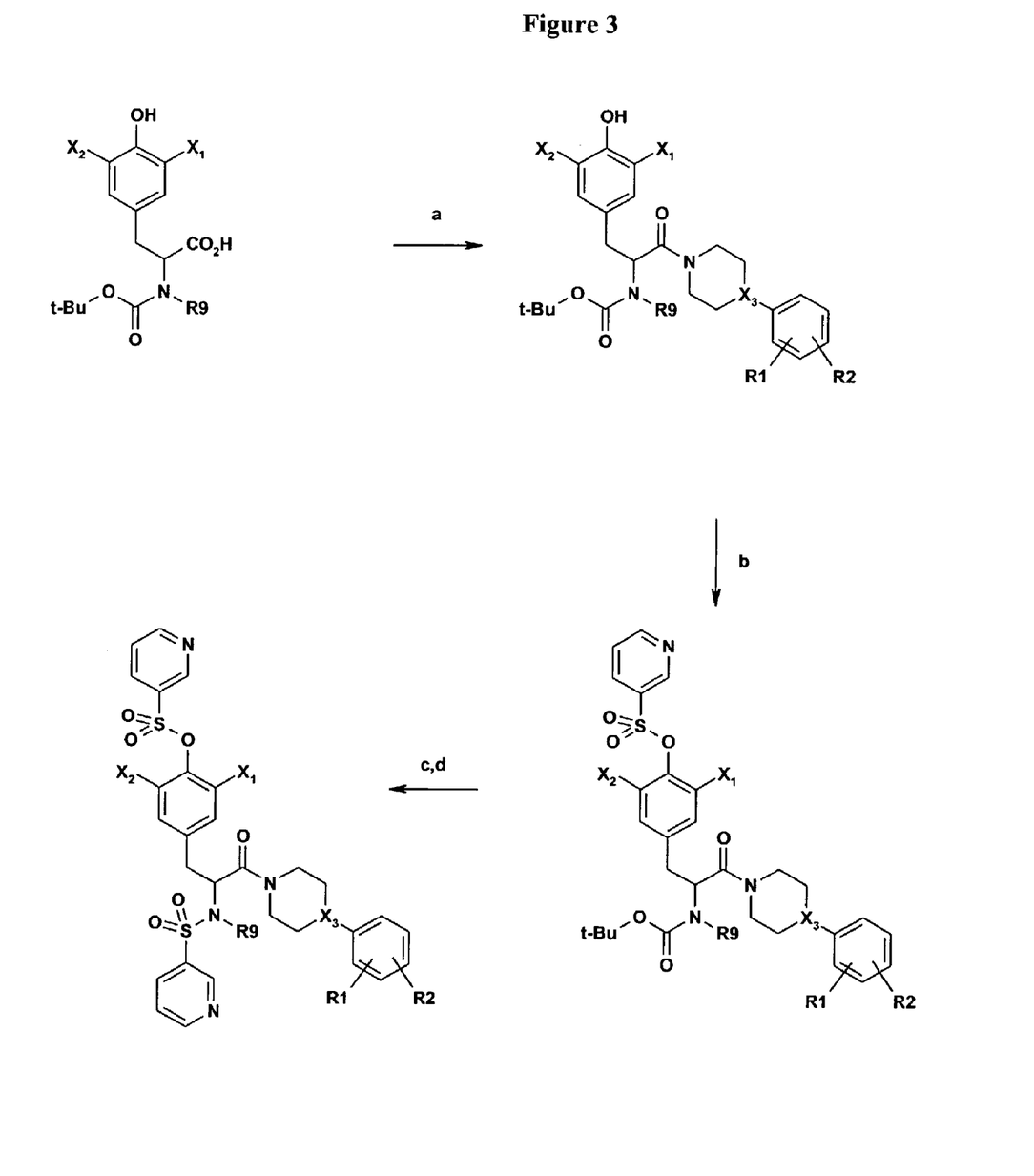
FIG. 3 illustrates the general synthesis procedure for compounds of formula III.

FIG. 3 illustrates the synthetic scheme followed in the preparation of compounds of Formula III and their intermediates. These compounds are prepared from an appropriately substituted N-Boc-protected-tyrosine. These precursors are converted to the activated 1-hydroxy-1,2,3-benzotriazole (HOBt) esters with HOBt and EDC and coupled with the desired substituted-N-arylpiperazines to provide the requisite amides in good yields. The phenolic anion of the tyrosyl-moiety compounds (generated in situ with sodium hydride) is converted to the corresponding 3-pyridinesulfonyl ester by treatment with a dichloromethane ($CH_2Cl_2$) solution of the requisite 3-pyridinesulfonyl chloride. Removal of the amine protecting tert-butyloxycarbonyl (Boc) group is conveniently effected with trifluoroacetic acid (TFA) in a $CH_2Cl_2$ solution to provide the corresponding free amine. This intermediate is then coupled with a excess of 3-pyridinesulfonyl chloride to provide the target products in acceptable yields. Reagents and conditions for the reactions referred to in FIG. 3: a. Substituted arylpiperazine or arylpiperidine, HOBt, EDC, DMF. b. Sodium hydride, pyridine-3-sulfonyl chloride, CH2Cl2. c. Trifluoroacetic acid, CH2Cl2. d. Triethylamine, pyridine-3-sulfonyl chloride, CH2Cl2.

Figure 4:
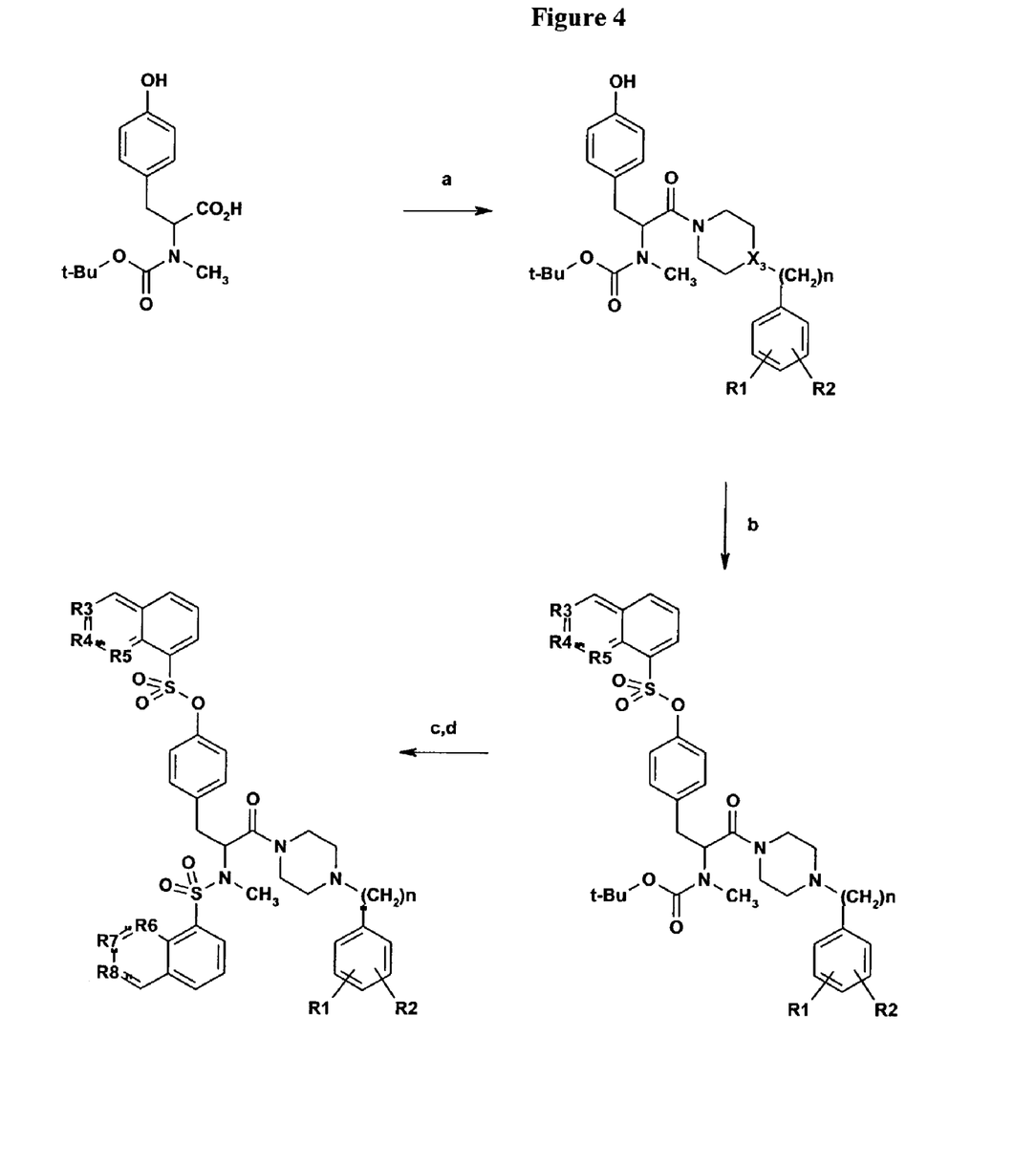
FIG. 4 illustrates the general synthesis procedure for compounds of formula IV.

FIG. 4 illustrates the synthetic process for the formation of the compounds of Formula IV and their intermediates. In summary, these compounds are prepared from an N-Boc-protected-tyrosine derivative. These amino-protected precursors are converted to the activated 1-hydroxy-1,2,3-benzotriazole (HOBt) esters with HOBt and EDC and coupled with the appropriate substituted-N-arylpiperazines or substituted-N-aralkylpiperazines, affording the requisite amides in good yields. The phenolic anion of the tyrosyl-moiety compounds (generated in situ with sodium hydride)

is converted to the corresponding heteroarylsulfonyl ester by treatment with a dichloromethane (CH2Cl2) solution of the requisite heteroarylsulfonyl chloride. Removal of the amine protecting tert-butyloxycarbonyl (Boc) group is conveniently effected with trifluoroacetic acid (TFA) in a CH2Cl2 solution to provide the corresponding free amine. This intermediate is then coupled with a excess of the desired heteroarylsulfonyl chloride to provide the desired sulphonamides in acceptable yields. Reagents and conditions for the reactions referred to in FIG. 4 are: a. Substituted aryl or aralkylpiperazine, HOBt, EDC, DMF. b. Sodium hydride, heteroarylsulfonyl chloride, CH2Cl2. c. Trifluoroacetic acid, CH2Cl2. d. Triethylamine, heteroarylsulfonyl chloride, CH2Cl2.

Where the plural form is used for compounds, and salts, this is taken to mean also a single compound or salt. Any asymmetric carbon atoms may be present in the (R)-, (S)- or (R, S) configuration. Substituents at a double bond or a ring may be present in cis-(Z) or trans (E) form. The compounds may thus be present as mixtures of isomers or as pure isomers. In cases wherein compounds may exist in tautomeric forms, each tautomeric form is contemplated as being included within this invention whether existing in equilibrium or predominantly in one form.

Certain of the compounds of the present invention are sufficiently basic, (e.g., amino derivatives) or acidic (e.g., carboxylic acid derivatives) to form salts. Pharmaceutically acceptable salts of the compounds of formulas I are within the scope of the present invention. As will be understood by those skilled in the art, pharmaceutically acceptable salts include, but are not limited, to salts with inorganic acids such as hydrochloride, sulfate, phosphate, hydrobromide, and nitrate or salts with an organic acid such as malate, maleate, fumarate, tartrate, succinate, citrate, acetate, lactate, methanesulfonate, p-toluenesulfonate, palmoate, salicylate, and stearate. Other acids such as oxalic, while not in themselves pharmaceutically acceptable, may be useful as intermediates in obtaining the compounds of the invention and their pharmaceutical salts.

Compounds with particularly significant $IC_{50}$ values would be useful for the identification and labeling of P2X receptors in mammals. This would make them useful as diagnostic agents for P2X receptors.

The compounds and their intermediates are formed in the following steps:

Step a. General Procedure for the Synthesis of Compounds $B_i$.

General procedure (A) for the synthesis of compounds $B_i$ of FIG. 1. To a solution of $A_i$ (1 mmole) in dry DMF (5 mL) cooled at 0° C. was added EDC (211 mg, 1.1 mmol, 1.1 equiv.), HOBt (1.1 mmol) and the suitable N-substituted piperazine (1.1 mmol). This mixture was stirred for 18 h and then concentrated in vacuo. The residue was dissolved in EtOAc (10 mL), washed with water (5 mL) and then with brine (5 mL). The organic layer was dried ($Na_2SO_4$) and concentrated in vacuo. The residue purified by column chromatography furnished the derivatives $B_i$.

1-[(S)—N-tert-butyloxycarbonyl-N-methyl-tyrosyl]-4-(benzyl)-piperazine. Following the general procedure (A), this product was obtained as a white solid (yield >95%); m.p.=104–106° C., [α]=−63.7, c=0.91% in $CHCl_3$. 1H-NMR ($CDCl_3$)δ: 1.36 (s, 9H), 2.28 (m, 4H), 2.79 (s, 3H), 2.83 (s, 2H), 2.89 (dd, J=16.7 and 7.3 Hz, 2H), 3.49 (m, 4H), 5.21 (t, J=7.3 Hz, 1H), 5.85 (s, 1H), 6.72 (d, J=8.3 Hz, 2H), 7.05 (d, J=8.3 Hz, 2H), 7.20 (m, 5H).

1-[(S)—N-tert-butyloxycarbonyl-N-methyl-tyrosyl]-4-(phenethyl)-piperazine. Following the general procedure (A), this product was obtained as a white solid (yield 46%); m.p.=1147–150° C., [α]=−46.8, c=1.5% in $CH_2Cl_2$. 1H-NMR ($CDCl_3$) δ: 1.37 (s, 9H), 2.38 (m, 4H), 2.58 (m, 2H), 2.75 (m, 2H), 2.81 (s, 3H), 2.89 (dd, J=14.1 and 8.3 Hz, 2H), 3.49 (m, 4H), 5.21 (t, J=8.3 Hz, 1H), 5.49 (s, 1H), 6.70 (d, J=8.3 Hz, 2H), 7.00 (d, J=8.3 Hz, 2H), 7.23 (m, 5H).

1-[(S)—N-tert-butyloxycarbonyl-N-methyl-tyrosyl]-4-(4-fluorophenyl)-piperazine. Following the general procedure (A), this product was obtained as a white solid (yield 94%); m.p.=67–69° C., [α]=−85.4, c=1.29% in $CHCl_3$. 1H-NMR ($CDCl_3$) δ: 1.34 (s, 9H), 2.78 (s, 3H), 2.89 (dd, J=16.7 and 7.3 Hz, 2H), 3.07 (m, 4H), 3.50 (m, 4H), 5.21 (t, J=7.3 Hz, 1H), 5.85 (s, 1H), 6.86 (m, 8H).

1-[(S)—N-tert-butyloxycarbonyl-N-methyl-tyrosyl]-4-(4-chlorophenyl)-piperazine. Following the general procedure (A), this product was obtained as a white solid (yield 78%); m.p.=73–75° C., [α]=−77, c=0.76% in $CHCl_3$. 1H-NMR ($CDCl_3$) δ: 1.39 (s, 9H), 1.56 (m, 2H), 2.89 (s, 3H), 2.95 (m, 4H), 3.54 (m, 4H), 5.25 (t, J=7.2 Hz, 1H), 6.78 (m, 3H), 7.02 (d, J=8.4 Hz, 1H), 7.09 (d, J=8.2 Hz, 2H), 7.22 (m, 2H), 9.46 (s, 1H).

1-[(S)—N-tert-butyloxycarbonyl-N-methyl-tyrosyl]-4-(4-iodophenyl)-piperazine. Following the general procedure (A), this product was obtained as a yellow solid (yield 92%); m.p.=73–75° C., [α]=−65.4, c=1.02% in $CHCl_3$. 1H-NMR ($CDCl_3$) δ: 1.38 (s, 9H), 2.82 (s, 3H), 2.93 (dd, J=14.6 and 7.2 Hz, 2H), 3.12 (m, 4H), 3.51 (m, 4H), 5.24 (t, J=7.2 Hz, 1H), 5.82 (s, 1H), 6.61 (d, J=8.8 Hz, 2H), 6.72 (d, J=8.4 Hz, 2H), 7.10 (d, J=8.4 Hz, 2H), 7.52 (d, J=8.8 Hz, 2H).

1-[(S)—N-tert-butyloxycarbonyl-N-methyl-tyrosyl]-4-(p-tolyl)-piperazine. Following the general procedure (A), this product was obtained as a foam oil (yield 93%); [α]=−83.3, c=1.34% in $CHCl_3$. 1H-NMR ($CDCl_3$) δ: 1.38 (s, 9H), 2.27 (s, 3H), 2.81 (s, 3H), 2.86 (dd, J=14 and 7.6 Hz, 2H), 3.42 (m, 4H), 3.54 (m, 4H), 5.26 (t, J=7 Hz, 1H), 6.80 (m, 4H), 7.06 (m, 4H), 9.5 (s, 1H).

1-[(S)—N-tert-butyloxycarbonyl-N-methyl-tyrosyl]-4-(4-methoxyphenyl)-piperazine. Following the general procedure (A), this product was obtained as a foam yellow solid (yield 89%); [α]=−63.3, c=1.1% in $CHCl_3$. 1H-NMR ($CDCl_3$) δ: 1.38 (s, 9H), 2.82 (s, 3H), 2.87 (m, 6H), 3.52 (m, 4H), 3.77 (s, 3H), 5.26 (t, J=7.2 Hz, 1H), 6.71 (d, J=8.4 Hz, 2H), 6.84 (m, 2H), 7.02 (d, J=8.6 Hz, 2H), 7.10 (d, J=8.6 Hz, 2H), 9.46 (s, 1H).

1-[(S)—N-tert-butyloxycarbonyl-N-methyl-tyrosyl]-4-(4-nitrophenyl)-piperazine. Following the general procedure (A), this product was obtained as a yellow solid (yield 88%); m.p.=211–213° C., [α]=−66.7, c=1.02% in $CHCl_3$. 1H-NMR ($CDCl_3$) δ: 1.39 (s, 9H), 2.74 (dd, J=14 and 7.6 Hz, 2H), 2.84 (s, 3H), 3.34 (m, 4H), 3.56 (m, 4H), 5.25 (t, J=7.2 Hz, 1H), 6.71 (d, J=3.4 Hz, 2H), 6.76 (d, J=3.4 Hz, 2H), 7.12 (d, J=8.4 Hz, 2H), 8.12 (d, J=9.2 Hz, 2H). 9.5 (s, 1H).

1-[(S)—N-tert-butyloxycarbonyl-N-methyl-tyrosyl]-4-(4-cyanophenyl)-piperazine. Following the general procedure (A), this product was obtained as a oil (yield 76%); [α]=−49.7, c=1.47% in $CHCl_3$. 1H-NMR ($CDCl_3$) δ: 1.39 (s, 9H), 1.56 (m, 2H), 2.84 (s, 3H), 3.10 (m, 4H), 3.52 (m, 4H), 5.31 (t, J=7.2 Hz, 1H), 6.73 (d, J=8.6 Hz, 2H), 6.79 (d, J=9.2 Hz, 2H), 7.11 (d, J=8.2 Hz, 2H), 7.48 (d, J=8.8 Hz, 2H), 9.46 (s, 1H).

1-[(S)—N-tert-butyloxycarbonyl-N-methyl-tyrosyl]-4-(4-acetylphenyl)-piperazine. Following the general procedure (A), this product was obtained as a yellow solid (yield); m.p.=° C., [α]=.1H-NMR ($CDCl_3$) δ: 1.34 (s, 9H), 2.53 (s, 3H), 2.84 (s, 3H), 2.93 (dd, J=14.8 and 7.3 Hz, 2H), 3.42 (m, 4H), 3.54 (m, 4H), 5.26 (t, J=7.3 Hz, 1H), 5.91 (s, 1H), 6.77 (m, J=8 Hz, 4H), 7.10 (d, J=8 Hz, 2H), 7.87 (d, J=8 Hz, 2H).

1-[(S)—N-tert-butyloxycarbonyl-N-methyl-tyrosyl]-4-(4-fluorobenzyl)-piperazine. Following the general procedure (A), this product was obtained as a brown oil (yield 78%); [α]=−62.2, c=0.49% in CHCl$_3$. 1H-NMR (CDCl$_3$) δ: 1.37 (s, 9H), 2.37 (m, 4H), 2.84 (s, 5H), 2.94 (m, 1H), 3.11 (m, 1H), 3.53 (m, 4H), 4.57 (m, 1H), 5.16 (t, J=7.3 Hz, 1H), 6.78 (d, J=8.1 Hz, 2H), 7.00 (m, J=8.4 Hz, 4H), 7.21 (d, J=8.2 Hz, 2H).

1-[(S)—N-tert-butyloxycarbonyl-N-methyl-tyrosyl]-4-(4-fluorobenzoyl)-piperazine. Following the general procedure (A), this product was obtained as a white oil (yield 97%); [α]=−10.6, c=1.18% in CH$_2$Cl$_2$. 1H-NMR (CDCl$_3$) δ: 1.38 (s, 9H), 2.85 (s, 3H), 3.00 (m, 2H), 3.50 (m, 8H), 4.57 (m, 1H), 5.16 (m, 1H), 6.73 (d, J=8.3 Hz, 2H), 7.08 (m, 4H), 7.38 (d, J=8.2 Hz, 2H).

1-[(S)—N-tert-butyloxycarbonyl-N-methyl-tyrosyl]-4-(4-nitrobenzyl)-piperazine. Following the general procedure (A), this product was obtained as a brown oil (yield 78%); [α]=−30, c=0.46% in CHCl$_3$. 1H-NMR (CDCl$_3$) δ: 1.35 (s, 9H), 2.35 (m, 4H), 2.82 (s, 2H), 2.89 (m, 2H), 2.96 (s, 3H), 3.51 (m, 4H), 4.88 (m, 1H), 5.19 (m, 1H), 6.75 (d, J=8.5 Hz, 2H), 7.05 (d, J=8.5 Hz, 2H), 7.46 (d, J=8.3 Hz, 2H), 8.14 (d, J=8.3 Hz, 2H).

1-[(S)—N-tert-butyloxycarbonyl-N-methyl-tyrosyl]-4-(2-fluorophenyl)-piperazine. Following the general procedure (A), this product was obtained as a white solid (yield 78%); m.p.=73–75° C., [α]=−77, c=0.76% in CHCl$_3$. 1H-NMR (CDCl$_3$) δ: 1.38 (s, 9H), 2.84 (s, 3H), 2.94 (m, 4H), 3.11 (dd, J=13.8 and 7.6 Hz, 2H), 3.58 (m, 4H), 5.26 (t, J=7.2 Hz, 1H), 6.76 (m, 3H), 7.01 (m, 5H), 9.46 (s, 1H).

1-[(S)—N-tert-butyloxycarbonyl-N-methyl-tyrosyl]-4-(2-chlorophenyl)-piperazine. Following the general procedure (A), this product was obtained as a white solid (yield >95%); m.p.=70–72° C., [α]=−70.3, c=1.15% in CHCl$_3$. 1H-NMR (CDCl$_3$) δ: 1.38 (s, 9H), 2.84 (s, 3H), 2.91 (m, 6H), 3.71 (m, 4H), 5.25 (t, J=7.2 Hz, 1H), 5.82 (s, 1H), 6.74 (m, 2H), 7.04 (m, 5H), 7.34 (d, J=9.2, Hz 1H).

1-[(S)—N-tert-butyloxycarbonyl-N-methyl-tyrosyl]-4-(o-tolyl)-piperazine. Following the general procedure (A), this product was obtained as a white solid (yield 95%); m.p.=80–82° C., [α]=−66.7, c=1.9% in CHCl$_3$. 1H-NMR (CDCl$_3$) δ: 1.38 (s, 9H), 2.28 (s, 3H), 2.74 (m, 6H), 2.86 (s, 3H), 3.65 (m, 4H), 5.26 (t, J=7.2 Hz, 1H), 6.01 (s, 1H), 6.74 (m, 2H), 7.10 (m, 6H).

1-[(S)—N-tert-butyloxycarbonyl-N-methyl-tyrosyl]-4-(2-methoxyphenyl)-piperazine. Following the general procedure (A), this product was obtained as a white solid (yield >95%); m.p.=153–155° C., [α]=−126.9, c=0.93% in CHCl$_3$. 1H-NMR (CDCl$_3$) δ: 1.38 (s, 9H), 2.83 (s, 3H), 2.93 (m, 6H), 3.64 (m, 4H), 3.86 (s, 3H), 5.27 (t, J=7.2 Hz, 1H), 5.82 (s, 1H), 6.72 (m, 3H), 6.89 (m, 2H), 7.06 (m, 3H).

1-[(S)—N-tert-butyloxycarbonyl-N-methyl-tyrosyl]-4-(3-chlorophenyl)-piperazine. Following the general procedure (A), this product was obtained as a yellow solid (yield 93%); m.p.=60–62° C., [α]=−72, c=0.88% in CHCl$_3$. 1H-NMR (CDCl$_3$) δ: 1.36 (s, 9H), 2.83 (s, 3H), 2.99 (m, 6H), 3.52 (m, 4H), 5.26 (t, J=7.2 Hz, 1H), 6.76 (m, 4H), 7.12 (m, 4H), 9.46 (s, 1H).

1-[(S)—N-tert-butyloxycarbonyl-N-methyl-tyrosyl]-4-(3-trifluoromethyl-phenyl)-piperazine (27). Following the general procedure (A), this product was obtained as a yellow solid (yield 78%); m.p.=102–104° C., [α]=−63.4, c=0.8% in CHCl$_3$. 1H-NMR (CDCl$_3$) δ: 1.39 (s, 9H), 2.83 (s, 3H), 3.04 (m, 6H), 3.56 (m, 4H), 5.25 (t, J=7.2 Hz, 1H), 5.82 (s, 1H), 6.73 (d, J=8.3 Hz, 2H), 7.02 (m, 3H), 7.10 (d, J=8.3 Hz, 2H), 7.35 (m, 1H).

1-[(S)—N-tert-butyloxycarbonyl-N-methyl-tyrosyl]-4-(2,3-dimethylphenyl)-piperazine. Following the general procedure (A), this product was obtained as a oil (yield 91%); [α]=−20.3, c=0.7% in CH$_2$Cl$_2$. 1H-NMR (CDCl$_3$) δ: 1.44 (s, 9H), 2.18 (s, 3H), 2.26 (s, 3H), 2.85 (s, 3H), 2.93 (m, 6H), 3.65 (m, 4H), 5.25 (t, J=7.2 Hz, 1H), 5.82 (s, 1H), 6.76 (m, 3H), 6.94 (m, 1H), 7.06 (m, 3H).

1-[(S)—N-tert-butyloxycarbonyl-N-methyl-tyrosyl]-4-(3,4-dichlorophenyl)-piperazine Following the general procedure (A), this product was obtained as a white solid (yield 85%); m.p.=77–78° C., [α]=−71.4, c=0.42% in CHCl$_3$. 1H-NMR (CDCl$_3$) δ: 1.39 (s, 9H), 2.84 (s, 3H), 2.99 (m, 6H), 3.56 (m, 4H), 5.25 (t, J=7.2 Hz, 1H), 6.75 (m, 2H), 6.88 (m, 1H), 7.08 (m, 2H), 7.26 (m, 2H), 9.46 (s, 1H).

1-[(S)—N-tert-butyloxycarbonyl-N-methyl-tyrosyl]-4-(pyridin-2-yl)-piperazine. Following the general procedure (A), this product was obtained as a white oil (yield 89%); [α]=−57.1, c=0.7% in CH$_2$Cl$_2$. 1H-NMR (CDCl$_3$) δ: 1.39 (s, 9H), 2.83 (s, 3H), 2.97 (m, J=7.6 Hz, 1H), 3.50 (m, 9H), 4.95 (m, 1H), 5.26 (t, J=7.5 Hz, 1H), 6.66 (m, J=8.6 Hz, 4H), 7.05 (m, J=8.3 Hz, 2H), 7.49 (m, 1H), 8.18 (m, 1H).

1-[(S)—N-tert-butyloxycarbonyl-N-methyl-tyrosyl]-4-(pyrimidin-2-yl)-piperazine. Following the general procedure (A), this product was obtained as a white solid (yield 91%); m.p.=109–111° C., [α]=−54.5, c=0.27% in CH$_2$Cl$_2$. 1H-NMR (CDCl$_3$) δ: 1.38 (s, 9H), 2.83 (s, 3H), 3.02 (m, 2H), 3.53 (m, 5H), 3.88 (m, 3H), 4.92 (m, 1H), 5.26 (t, J=7.5 Hz, 1H), 6.53 (m, 1H), 6.72 (m, 2H), 7.09 (m, J=8.3 Hz, 2H), 8.32 (m, 1H).

1-[(S)—N-tert-butyloxycarbonyl-N-methyl-tyrosyl]-4-(benzyl)-piperidine. Following the general procedure (A), this product was obtained as a white solid (yield >95%); m.p.=70–72° C., [α]=−61.7, c=0.46% in CH$_2$Cl$_2$. 1H-NMR (CDCl$_3$) δ: 1.39 (s, 9H), 1.62 (m, 5H), 2.50 (m, 3H), 2.86 (m, J=12.6 and 6.8 Hz, 6H), 3.95 (m, 1H), 4.58 (m, 1H), 5.21 (t, J=6.8 Hz, 1H), 5.85 (s, 1H), 6.72 (m, J=7.5 Hz, 2H), 7.10 (m, 4H), 7.25 (m, 3H).

1-[(S)—N-tert-butyloxycarbonyl-tyrosyl]-4-(4-fluorophenyl)-piperazine. Following the general procedure (A), this product was obtained as a foam yellow oil (yield 87%); [α]=+7.0, c=0.43% in CH$_2$Cl$_2$. 1H-NMR (CDCl$_3$) δ: 1.43 (s, 9H), 2.93 (m, 6H), 3.57 (m, 4H), 4.82 (t, J=8.6 Hz, 1H), 5.45(s, 1H), 6.75 (m, 4H), 6.93 (d, J=8.4 Hz, 2H), 7.04 (d, J=8.4 Hz, 2H).

1-[(S)—N-tert-butyloxycarbonyl-tyrosyl]-4-(o-tolyl)-piperazine. Following the general procedure (A), this product was obtained as a white solid (yield 94%); m.p.=80–82° C., [α]=+14.9, c=1.03% in CH$_2$Cl$_2$. 1H-NMR (CDCl$_3$) δ: 1.43 (s, 9H), 2.26 (s, 3H), 2.31 (m, 1H), 2.69 (m, 3H), 2.92 (d, J=6.9 Hz, 2H), 3.29 (m, 1H), 3.46 (m, 1H), 3.69 (m, 2H), 4.85 (dd, J=15.7 and 7.3 Hz, 1H), 5.47 (d, J=8.6 Hz, 1H), 6.20 (s, 1H), 6.74 (d, J=8.4 Hz, 2H), 6.86 (d, J=7.7 Hz, 1H), 7.03 (m, J=8.4 Hz, 3H), 7.15 (t, J=7.4 Hz, 2H).

[2-(3,4-Dihydro-1H-pyrazino[1,2-a]indol-2-yl)-1-(4-hydroxy-benzyl)-2-oxo-ethyl]-carbamic acid tert-butyl ester. Following the general procedure (A) this product was obtained. m.p. 85–87° C.; [a]=−4.1, c=0.9% in CHCl3; 1H-NMR (CDCl3): d 1.44 (s, 9H), 2.90 (t, J=4 Hz, 2H), 3.52 (m, 1H), 3.81 (m, 3H), 4.43 (m, 1H), 4.86 (m, 2H), 5.43 (d, J=10.8 Hz, 1H), 5.65 (s, 1H), 6.1 (s, 1H), 6.54 (d, J=6.8 Hz, 2H), 6.96 (dd, J=8.2 and 5.8 Hz, 2H), 7.129 (m, 3H), 7.56 (d, J=8.0 Hz, 1H).

[2-(3,4-Dihydro-1H-pyrazino[1,2-a]indol-2-yl)-1-(4-hydroxy-benzyl)-2-oxo-ethyl]-methyl-carbamic acid tert-butyl ester. Following the general procedure (A) this product was obtained. m.p. 130–132° C.; [a]=−9.47, c=0.35% in CHCl3; 1H-NMR (CDCl3): d 1.42 (s, 9H), 2.71 (s, 3H), 2.82 (t, J=4.0 Hz, 2H), 3.96 (m, 4H), 4.43 (m, 1H), 4.84 (m, 2H), 5.33 (d, J=10.6 Hz, 1H), 5.43 (t, J=7.2 Hz, 1H), 6.34 (dd, J=12.2 and 7.2 Hz, 1H), 6.64 (m, 1H), 7.15 (m, 5H), 7.57 (d, J=8.2 Hz, 1H).

[2-(8-Fluoro-3,4-dihydro-1H-pyrazino[1,2-a]indol-2-yl)-1-(4-hydroxy-benzyl)-2-oxo-ethyl]-methyl-carbamic acid tert-butyl ester. Following the general procedure (A) this product was obtained. m.p. 65–67° C.; [a]=−79.3, c=1% in CHCl3; 1H-NMR (CDCl3): d 1.41 (s, 9H), 2.84 (s, 3H), 2.96 (m, 2H), 4.15 (m, 4H), 4.84 (t, J=14.6 Hz, 1H), 5.02 (t, J=14.6 Hz, 1H), 5.37 (d, J=8.6 Hz, 1H), 5.53 (d, J=6.2 Hz, 1H), 6.26 (dd, J=12.0 and 7.2 Hz, 1H), 6.73 (m, 2H), 7.13 (m, 5H).

General procedure (B) for the synthesis of compounds $C_i$. To a suspension of NaH (24 mg of 55–65% oil suspension, 0.6 mmol, 1.2 equiv.) in dry THF (5 mL) was added $B_i$ (0.5 mmol, 1 equiv.). After 10', the isoquinoline sulfonyl chloride (1 mmole, 2 equiv.) dissolved in dry DCM (2 mL) was added. This mixture was stirred for 18 h at rt. and then concentrated in vacuo. The residue was dissolved in a mixture of EtOAc (10 mL) and a saturated aqueous NaHCO$_3$ (5 mL). After the layers were separated, the organic layer was dried (Na$_2$SO$_4$), concentrated in vacuo and the residue purified by column chromatography yielded the derivatives $C_i$.

1-[(S)—O-isoquinolinesulfonyl-N-tert-butyloxycarbonyl-N-methyl-tyrosyl]-4-(benzyl)-piperazine. Following the general procedure (B), this product was obtained as a yellow oil (yield 90%); [α]=−64.4, c=1.15% in CHCl$_3$. 1H-NMR (CDCl$_3$) δ: 1.31 (s, 9H), 2.72 (m, 4H), 2.90 (m, 2H), 3.48 (m, 7H), 3.70 (m, 2H), 5.15 (t, J=7 Hz, 1H), 6.76 (m, J=8.6 Hz, 3H), 7.05 (m, J=8.6 Hz, 3H), 7.28 (m, 3H), 7.63 (m, 1H), 8.27 (m, J=7.8 Hz, 2H), 8.54 (d, J=6.1 Hz, 1H), 8.79 (d, J=6.1 Hz, 1H), 9.42 (s, 1H).

1-[(S)—O-isoquinolinesulfonyl-N-tert-butyloxycarbonyl-N-methyl-tyrosyl]-4-(phenethyl)-piperazine. Following the general procedure (B), this product was obtained as a white solid (yield 82%); m.p.=58–60° C., [α]=−33.8, c=0.73% in CH$_2$Cl$_2$. 1H-NMR (CDCl$_3$) δ: 1.39 (s, 9H), 2.05 (s, 1H), 2.17 (s, 1H), 2.39 (m, 3H), 2.57 (m, 3H), 2.72 (m, 4H), 2.87 (m, 2H), 3.36 (m, 2H), 3.51 (m, 1H), 5.15 (t, J=7 Hz, 1H), 6.77 (m, 2H), 7.03 (d, J=8.3 Hz, 2H), 7.18 (m, 3H), 7.25 (m, 2H), 7.59 (m, J=8.0 Hz, 1H), 8.25 (m, J=5.8 Hz, 2H), 8.53 (d, J=6.2 Hz, 1H), 8.79 (d, J=6.2 Hz, 1H), 9.42 (s, 1H).

1-[(S)—O-isoquinolinesulfonyl-N-tert-butyloxycarbonyl-N-methyl-tyrosyl]-4-(4-fluorophenyl)-piperazine. Following the general procedure (B), this product was obtained as a oil (yield 85%); [α]=−54.1, c=1.31% in CHCl$_3$. 1H-NMR (CDCl$_3$) δ: 1.33 (s, 9H), 2.73 (s, 3H), 2.91 (m, 6H), 3.51 (m, 4H), 5.17 (t, J=7.2 Hz, 1H), 6. (m, J=8.6 Hz, 4H), 7.01 (m, J=8.6 Hz, 4H), 7.62 (dd, J=7.6 Hz, 1H), 8.26 (m, J=7.6, 2H), 8.52 (d, J=6.1 Hz, 1H), 8.79 (d, J=6.1 Hz, 1H), 9.40 (s, 1H).

1-[(S)—O-isoquinolinesulfonyl-N-tert-butyloxyarbonyl-N-methyl-tyrosyl]-4-(4-chlorophenyl)-piperazine. Following the general procedure (B), this product was obtained as a white liquid (yield 86%); [α]=−68.4, c=1% in CHCl$_3$. 1H-NMR (CDCl$_3$) δ: 1.33 (s, 9H), 1.57 (m, 2H), 2.74 (s, 3H), 3.09 (m, 4H), 3.48 (m, 4H), 5.22 (t, J=7 Hz, 1H), 6.77 (m, 4H), 7.10 (t, J=8.6 Hz, 2H), 7.23 (m, 2H), 7.61 (t, J=8.6 Hz, 1H), 8.25 (dd, J=6.6 and 6.2 Hz, 2H), 8.54 (d, J=6.2 Hz, 1H), 8.80 (d, J=6.2 Hz, 1H), 9.41 (s, 1H).

1-[(S)—O-isoquinolinesulfonyl-N-tert-butyloxyarbonyl-N-methyl-tyrosyl]-4-(4-iodophenyl)-piperazine. Following the general procedure (B), this product was obtained as a foam yellow oil (yield >95%); [α]=−48.8, c=1.22% in CHCl$_3$. 1H-NMR (CDCl$_3$) δ: 1.34 (s, 9H), 2.73 (s, 3H), 2.98 (m, 6H), 3.51 (m, 4H), 5.21 (t, J=7 Hz, 1H), 6.64 (d, J=8.8, 2H), 6.76 (t, J=8.6, 2H), 7.09 (t, J=8.6, 2H), 7.53 (d, J=8.8, 2H), 7.61 (m, J=7.2 Hz, 1H), 8.25 (m, J=7.2 Hz, 2H), 8.53 (d, J=6.1 Hz, 1H), 8.80 (d, J=6.1 Hz, 1H), 9.41 (s, 1H).

1-[(S)—O-isoquinolinesulfonyl-N-tert-butyloxycarbonyl-N-methyl-tyrosyl]-4-(p-tolyl)piperazine. Following the general procedure (B), this product was obtained as a yellow oil (yield 90%); [α]=−10.9, c=1.34% in CHCl$_3$. 1H-NMR (CDCl$_3$) δ: 1.33 (s, 9H), 2.05 (s, 3H), 2.74 (s, 3H), 2.82 (m, 2H), 3.04 (m, 4H), 3.51 (m, 4H), 5.22 (t, J=7.2 Hz, 1H), 6.79 (t, J=8.4 Hz, 4H), 7.09 (d, J=8.4 Hz, 4H), 7.61 (t, J=7.6 Hz, 1H), 8.26 (m, 2H), 8.53 (d, J=6 Hz, 1H), 8.80 (d, J=6 Hz, 1H), 9.41 (s, 1H).

1-[(S)—O-isoquinolinesulfonyl-N-tert-butyloxycarbonyl-N-methyl-tyrosyl4-(4-methoxyphenyl)-piperazine. Following the general procedure (B), this product was obtained as a yellow oil (yield 82%); [α]=−63.3, c=1.1% in CHCl$_3$. 1H-NMR (CDCl$_3$) δ: 1.33 (s, 9H), 1.57 (m, 2H), 2.73 (s, 3H), 2.96 (m, 4H), 3.51 (m, 4H), 3.76 (s, 3H), 5.21 (t, J=7 Hz, 1H), 6.82 (m, 4H), 7.10 (t, J=8.6 Hz, 2H), 7.23 (m, 2H), 7.61 (t, J=8.6 Hz, 1H), 8.25 (dd, J=6.6 and 6.2 Hz, 2H), 8.54 (d, J=6.2 Hz, 1H), 8.78 (d, J=6.2 Hz, 1H), 9.42 (s, 1H).

1-[(S)—O-isoquinolinesulfonyl-N-tert-butyloxycarbonyl-N-methyl-tyrosyl]4-(4-nitrophenyl)-piperazine. Following the general procedure (B), this product was obtained as a yellow solid (yield 79%); m.p.=46–47° C., [α]=−58.71, c=1.01% in CHCl$_3$. 1H-NMR (CDCl$_3$) δ: 1.34 (s, 9H), 2.83 (dd, J=14 and 6.4 Hz, 2H), 2.95 (s, 3H), 3.44 (m, 4H), 3.56 (m, 4H), 5.19 (t, J=7.2 Hz, 1H), 6.79 (dd, J=7.2 and 3.6 Hz, 4H), 7.10 (d, J=8.6 Hz, 2H), 7.61 (t, J=7.8 Hz, 1H), 8.11 (d, J=7.4 Hz, 2H), 8.25 (t, J=8.8 Hz, 2H), 8.51 (d, J=6.2 Hz, 1H), 8.80 (d, J=6.2 Hz, 1H), 9.51 (s, 1H).

1-[(S)—O-isoquinolinesulfonyl-N-tert-butyloxycarbonyl-N-methyl-tyrosyl]4-(4-cyanophenyl)-piperazine. Following the general procedure (B), this product was obtained as a foal yellow oil (yield <95%); [α]=+4.21, c=1.4% in CHCl$_3$. 1H-NMR (CDCl$_3$) δ: 1.34 (s, 9H), 2.74 (s, 3H), 3.09 (m, 6H), 3.49 (m, 4H), 5.22 (t, J=7 Hz, 1H), 6.79 (t, J=8.6 Hz, 4H), 7.11 (t, J=8.4 Hz, 3H), 7.51 (d, J=8.6 Hz, 1H), 7.63 (t, J=7.6 Hz, 1H), 8.26 (dd, J=6.8 and 4.4 Hz, 2H), 8.51 (d, J=6 Hz, 1H), 8.80 (d, J=6 Hz, 1H), 9.41. (s, 1H).

1-[(S)—O-isoquinolinesulfonyl-N-tert-butyloxycarbonyl-N-methyl-tyrosyl]-4-(4-acetylphenyl)-piperazine. Following the general procedure (B), this product was obtained as a oil (yield >95%); [α]=−51.82, c=1.2% in CHCl$_3$. 1H-NMR (CDCl$_3$) δ: 1.35 (s, 9H), 2.53 (s, 3H), 2.74 (s, 3H), 3.49 (m, 10H), 5.19 (t, J=7.2 Hz, 1H), 6.77 (m, J=8.6 Hz, 2H), 6.84 (m, J=8.9 Hz, 2H), 7.10 (t, J=8.6 Hz, 2H), 7.62 (t, 1H), 7.89 (d, J=8.9 Hz, 2H), 8.28 (m, J=6.2 Hz, 2H), 8.51 (d, J=6.2 Hz, 1H), 8.80 (d, J=6.2 Hz, 1H), 9.42 (s, 1H).

1-[(S)—O-isoquinolinesulfonyl-N-tert-butyloxycarbonyl-N-methyl-tyrosyl]4-(4-fluorobenzyl)-piperazine. Following the general procedure (B), this product was obtained as a brown oil (yield 77%); [α]=−38.9, c=0.66% in CHCl$_3$. 1H-NMR (CDCl$_3$) δ: 1.32 (s, 9H), 2.72 (s, 3H), 2.90 (m, 3H), 3.50 (m, 7H), 3.73 (m, 2H), 5.15 (t, J=7 Hz, 1H), 6.78 (t, J=8.6 Hz, 2H), 7.03 (m, J=8.6 Hz, 4H), 7.25 (m, J=6.6 Hz, 2H), 7.64 (m, 1H), 8.28 (d, J=7.8 Hz, 2H), 8.54 (d, J=6.1 Hz, 2H), 8.81 (d, J=6.2 Hz, 1H), 9.42 (s, 1H).

1-[(S)—O-isoquinolinesulfonyl-N-tert-butyloxycarbonyl-N-methyl-tyrosyl]-4-(4-fluorobenzoyl)-piperazine. Following the general procedure (B), this product was obtained as a white oil (yield >95%); [α]=−27.4, c=0.74% in $CH_2Cl_2$. 1H-NMR ($CDCl_3$) δ: 1.35 (s, 9H), 1.62 (m, 5H), 2.50 (m, 3H), 2.72 (s, 3H), 2.90 (m, 3H), 3.90 (m, 1H), 4.50 (m, 1H), 5.12 (t, J=6.2 Hz, 1H), 6.76 (d, J=8.4 Hz, 2H), 7.08 (m, J=8.6 Hz, 4H), 7.23 (m, 3H), 7.67 (m, 1H), 8.27 (m, J=6.0 Hz, 2H), 8.54 (d, J=6.1 Hz, 1H), 8.80 (d, J=6.0 Hz, 1H), 9.42 (s, 1H).

1-[(S)—O-isoquinolinesulfonyl-N-tert-butyloxycarbonyl-N-methyl-tyrosyl]4-(4-nitrobenzyl)-piperazine. Following the general procedure (B), this product was obtained as a yellow oil (yield 54%); [α]=−44.5, c=0.44% in $CH_3OH$. 1H-NMR ($CDCl_3$) δ: 1.30 (s, 9H), 2.73 (m, 4H), 2.90 (m, 2H), 3.50 (m, 7H), 3.70 (m, 2H), 5.15 (t, J=7 Hz, 1H), 6.79 (t, J=8.3 Hz, 2H), 7.06 (t, J=8.5 Hz, 2H), 7.49 (d, J=8.3 Hz, 2H), 7.65 (t, J=7.7 Hz, 1H), 8.18 (d, J=8.3 Hz, 2H), 8.29 (d, J=7.7 Hz, 2H), 8.54 (d, J=6.0 Hz, 1H), 8.80 (d, J=6.1 Hz, 1H), 9.42 (s, 1H).

1-[(S)—O-isoquinolinesulfonyl-N-tert-butyloxycarbonyl-N-methyl-tyrosyl]-4-(2-fluorophenyl)-piperazine. Following the general procedure (B), this product was obtained as a yellow oil (yield >95%); [α]=−44.23, c=1.04% in $CHCl_3$. 1H-NMR ($CDCl_3$) δ: 1.34 (s, 9H), 2.75 (s, 3H), 2.92 (m, 6H), 3.52 (m, 4H), 5.22 (t, J=7 Hz, 1H), 6.79 (m, 5H), 7.14 (m, 4H), 7.62 (t, J=7.6 Hz, 1H), 8.26 (t, J=7.2 Hz, 1H), 8.53 (t, J=6 Hz, 1H), 8.82 (d, J=6 Hz, 1H), 9.41 (s, 1H).

[(S)—O-isoquinolinesulfonyl-N-tert-butyloxycarbonyl-N-methyl-tyrosyl-4-(2-chlorophenyl)-piperazine. Following the general procedure (B), this product was obtained as a oil (yield >95%); [α]=−40.6, c=1.23% in $CHCl_3$. 1H-NMR ($CDCl_3$) δ: 1.34 (s, 9H), 2.76 (s, 3H), 2.88 (m, 6H), 3.62 (m, 4H), 5.19 (t, J=7 Hz, 1H), 6.79 (t, J=8.6 Hz, 2H), 7.05 (m, J=6.2 and 8.6, 4H), 7.22 (d, J=6.2 Hz, 1H), 7.37 (d, J=7.9 Hz, 1H), 7.64 (t, 1H), 8.28 (t, J=7, 2H), 8.57 (d, J=6.1 Hz, 1H), 8.80 (d, J=6.1 Hz, 1H), 9.44 (s, 1H).

1-[(S)—O-Preparation of isoquinolinesulfonyl-N-tert-butyloxycarbonyl-N-methyl-tyrosyl]-4-(o-tolyl)-piperazine. Following the general procedure (B), this product was obtained as a yellow oil (yield 72%); [α]=−47.0, c=1.27% in $CHCl_3$. 1H-NMR ($CDCl_3$) δ: 1.38 (s, 9H), 2.28 (s, 3H), 2.74 (m, 6H), 2.86 (s, 3H), 3.65 (m, 4H), 5.26 (t, J=7.2 Hz, 1H), 6.81 (t, J=9.0 and 8.4 Hz, 3H), 7.02 (m, J=8.9 and 8.5 Hz, 3H), 7.18 (t, J=7.4 Hz, 2H), 7.72 (t, J=7.7 Hz, 1H), 8.27 (m, J=8.4 and 6.1 Hz, 2H), 8.54 (d, J=6 Hz, 1H), 8.82 (d, J=6 Hz, 1H), 9.43 (s, 1H).

1-[(S)—O-isoquinolinesulfonyl-N-tert-butyloxycarbonyl-N-methyl-tyrosyl]-4-(2-methoxyphenyl)-piperazine Following the general procedure (B), this product was obtained as a yellow oil (yield 64%); [α]=−61.0, c=1.54% in $CHCl_3$. 1H-NMR ($CDCl_3$) δ: 1.34 (s, 9H), 2.75 (s, 3H), 2.91 (m, 6H), 3.51 (m, 4H), 3.87 (s, 3H), 5.20 (t, J=7 Hz, 1H), 6.76 (d, J=8.5, 2H), 6.83 (m, J=6.6, 3H), 7.06 (m, J=8.5, 3H), 7.61 (m, J=6.6 Hz, 1H), 8.27 (m, 2H), 8.54 (d, J=6 Hz, 1H), 8.81 (d, J=6 Hz, 1H), 9.42 (s, 1H).

1-[(S)—O-isoquinolinesulfonyl-N-tert-butyloxycarbonyl-N-methyl-tyrosyl]-4-(3-chlorophenyl)-piperazine. Following the general procedure (B), this product was obtained as a foam yellow oil (yield >95%); m.p.=79–81° C., [α]=−42.2, c=0.62% in $CHCl_3$. 1H-NMR ($CDCl_3$) δ: 1.35 (s, 9H), 2.73 (s, 3H), 2.92 (m, 6H), 3.51 (m, 4H), 5.21 (t, J=7 Hz, 1H), 6.79 (m, 5H), 7.14 (m, 4H), 7.61 (t, J=7.2 Hz, 1H), 8.26 (t, J=7.2 Hz, 1H), 8.53 (d, J=6.2 Hz, 1H), 8.80 (d, J=4.2 Hz, 1H), 9.41 (s, 1H).

1-[(S)—O-isoquinolinesulfonyl-N-tert-butyloxycarbonyl-N-methyl-tyrosyl]-4-(3-trifluoromethylphenyl)-piperazine. Following the general procedure (B), this product was obtained as a white solid (yield 75%); m.p.=74–76° C., [α]=−48.9, c=0.76% in $CHCl_3$. 1H-NMR ($CDCl_3$) δ: 1.35 (s, 9H), 2.74 (s, 3H), 3.01 (m, 6H), 3.65 (m, 4H), 5.20 (t, J=7 Hz, 1H), 6.79 (m, J=8.6 Hz, 2H), 7.08 (m, J=8.6 Hz, 5H), 7.37 (t, J=7.8 Hz, 1H), 7.66 (m, J=7.8 Hz, 1H), 8.29 (dd, J=8.1 and 4.6 Hz, 2H), 8.58 (d, J=6.1 Hz, 1H), 8.81 (d, J=6.1 Hz, 1H), 9.44 (s, 1H).

1-[(S)—O-isoquinolinesulfonyl-N-tert-butyloxycarbonyl-N-methyl-tyrosyl]4-(2,3-dimethylphenyl)-piperazine. Following the general procedure (B), this product was obtained as a yellow oil (yield 44%); [α]=−70, c=0.2% in $CH_2Cl_2$. 1H-NMR ($CDCl_3$) δ: 1.39 (s, 9H), 2.21 (s, 3H), 2.27 (s, 3H), 2.76 (s, 3H), 2.82 (m, 6H), 3.58 (m, 4H), 5.20 (t, J=7 Hz, 1H), 6.80 (m, J=8.3 Hz, 3H), 6.95 (m, 1H), 7.08 (m, J=8.4 Hz, 3H), 7.66 (m, 1H), 8.26 (m, J=8.4 Hz, 2H), 8.55 (d, J=6.1 Hz, 1H), 8.81 (d, J=6.1 Hz, 1H), 9.41 (s, 1H).

1-[(S)—O-isoquinolinesulfonyl-N-tert-butyloxycarbonyl-N-methyl-tyrosyl-4-(3,4-dichlorophenyl)-piperazine. Following the general procedure (B), this product was obtained as a yellow solid (yield 52%); m.p.=85–87° C., [α]=+12, c=0.5% in $CHCl_3$. 1H-NMR ($CDCl_3$) δ: 1.34 (s, 9H), 2.73 (s, 3H), 2.92 (m, 6H), 3.51 (m, 4H), 5.19 (t, J=7 Hz, 1H), 6.74 (m, 2H), 6.90 (s, 1H), 7.10 (d, J=7.4 Hz, 1H), 7.32 (d, J=7.4 Hz, 1H), 7.63 (t, J=7.6 Hz, 1H), 8.26 (dd, J=7 and 3.6 Hz, 1H), 8.54 (t, J=6 Hz, 1H), 8.81 (d, J=6 Hz, 1H), 9.42 (s, 1H).

1-[(S)—O-isoquinolinesulfonyl-N-tert-butyloxycarbonyl-N-methyl-tyrosyl]4-(pyridin-2-yl)-piperazine. Following the general procedure (B), this product was obtained as a white solid (yield 90%); m.p.=56–58° C., [α]=−59.3, c=0.43% in $CH_2Cl_2$. 1H-NMR ($CDCl_3$) δ: 1.35 (s, 9H), 2.75 (s, 3H), 3.00 (m, 1H), 3.45 (m, 8H), 3.85 (m, 1H), 5.19 (t, J=7 Hz, 1H), 6.69 (m, J=8.4 Hz, 4H), 7.07 (t, J=8.4 Hz, 2H), 7.51 (t, J=6.6 Hz, 1H), 7.62 (m, 1H), 8.23 (m, J=7.1 Hz, 3H), 8.53 (d, J=6.1 Hz, 1H), 8.89 (d, J=6.2 Hz, 1H), 9.41 (s, 1H).

1-[(S)—O-isoquinolinesulfonyl-N-tert-butyloxycarbonyl-N-methyl-tyrosyl]4-(pyrimidin-2-yl)-piperazine]. Following the general procedure (B), this product was obtained as a white solid (yield 80%); m.p.=104–106° C., [α]=−48.6, c=0.37% in $CH_2Cl_2$. 1H-NMR ($CDCl_3$) δ: 1.35 (s, 9H), 2.76 (s, 3H), 3.00 (m, 2H), 3.53 (m, 5H), 3.85 (m, 3H), 5.19 (t, J=7 Hz, 1H), 6.54 (m, 1H), 6.78 (t, J=8.4 Hz, 2H), 7.08 (t, J=8.4 Hz, 2H), 7.63 (m, 1H), 8.29 (m, 4H), 8.53 (d, J=6.1 Hz, 1H), 8.81 (d, J=6.2 Hz, 1H), 9.42 (s, 1H).

1-[(S)—O-isoquinolinesulfonyl-N-tert-butyloxycarbonyl-N-methyl-tyrosyl]4-(benzyl)-piperidine]. Following the general procedure (B), this product was obtained as a white solid (yield 90%); m.p.=100–102° C., [α]=−39.3, c=0.4% in $CH_2Cl_2$. 1H-NMR ($CDCl_3$) δ: 1.31 (s, 9H), 2.72 (m, 4H), 2.90 (m, 2H), 3.48 (m, 7H), 3.70 (m, 2H), 5.15 (t, J=7 Hz, 1H), 6.76 (m, J=8.6 Hz, 3H), 7.05 (m, J=8.6 Hz, 3H), 7.28 (m, 3H), 7.63 (m, 1H), 8.27 (m, J=7.8 Hz, 2H), 8.54 (d, J=6.1 Hz, 1H), 8.79 (d, J=6.1 Hz, 1H), 9.42 (s, 1H).

1-[(S)—O-isoquinolinesulfonyl-N-tert-butyloxycarbonyl-tyrosyl]-4-(4-fluorophenyl)-piperazine. Following the general procedure (B), this product was obtained as a white solid (yield 79%); m.p.=87–89° C., [α]=−1.6, c=0.63% in $CH_2Cl_2$. 1H-NMR ($CDCl_3$) δ: 1.39 (s, 9H), 2.65 (m, 1H), 2.92 (m, 6H), 3.43 (m, 2H), 3.78 (m, 1H), 4.76 (m, 1H), 5.33 (d, 1H), 6.82 (m, 4H), 7.01 (m, 4H), 7.54 (t, J=7.6 Hz, 1H), 8.22 (dd, J=7.5 and 8.2 Hz, 2H), 8.53 (d, J=6.1 Hz, 1H), 8.80 (d, J=6.1 Hz, 1H), 9.41 (s, 1H).

1-[(S)—O-isoquinolinesulfonyl-N-tert-butyloxycarbonyl-tyrosyl]-4-(o-tolyl)-piperazine. Following the general procedure (B), this product was obtained as a white solid (yield 73%); m.p.=73–75° C., [α]=+22.5, c=1.3% in $CH_2Cl_2$. 1H-NMR ($CDCl_3$) δ: 1.39 (s, 9H), 2.27 (s, 3H), 2.42 (m, 1H), 2.75 (m, 3H), 2.91 (d, J=6.7 Hz, 2H), 3.15 (m, 3H), 3.51 (m, 3H), 4.80 (m, 1H), 5.37 (d, J=8.5 Hz, 1H), 6.80 (d, J=8.5 Hz, 2H), 6.90 (d, J=7.8 Hz, 1H), 7.05 (t, J=8.4

Hz, 3H), 7.18 (t, J=7.3 Hz, 2H), 7.54 (t, J=7.8, 1H), 8.22 (dd, J=8.2 and 7.3 Hz, 2H), 8.54 (d, J=6.2 Hz, 1H), 8.81 (d, J=6 Hz, 1H), 9.41 (s, 1H).

General procedure for removal the Boc protecting group from compounds $C_i$. The ester $C_i$ (1.5 mmol) was stirred at rt. in a mixture of TFA/CH$_2$Cl$_2$ (1:1, 5 mL) for 3 h. The volatiles were removed in vacuo and the residue was diluted with 5% aqueous NaHCO$_3$ (5 mL). The aqueous mixture was extracted with CH$_2$Cl$_2$ (3×5 mL) and the combined organic extracts were dried (Na$_2$SO$_4$) and concentrated in vacuo. The residue obtained was used for the next reaction without any purification.

General procedure (C) for the synthesis of compounds $D_i$. To a stirred solution of the appropriate free amine (0.5 mmol) in dry DCM (5 mL) were added Et$_3$N (70 µL, 0.5 mmol, 1 equiv.) and then dropwise isoquinolinesulfonyl chloride (1 mmole, 2 equiv.) dissolved in DCM (3 mL), under cooling with ice. The reaction mixture obtained was allowed to slowly warm up to rt. and stirred for 18 h. After this time, the mixture was diluted with DCM (5 mL) and washed with a saturated aqueous NaHCO$_3$ (2 mL), water (5 mL) and brine (5 mL). After the layers were separated, the organic layer was dried (Na$_2$SO$_4$) and concentrated in vacuo. The residue obtained, subjected to purification by column chromatography, furnished the appropriate product $D_i$.

Preparation of 1-[(S)—N,O-bis-(isoquinolinesulfonyl)-N-methyl-tyrosyl]-4-(benzyl)piperazine. Following the general procedure (C), this product was obtained as a yellow solid (yield 35%); m.p.=92–94° C., [α]=−33.8, c=0.95% in CHCl$_3$. 1H-NMR (CDCl$_3$) δ: 1.95 (m, 1H), 2.16 (m, 1H), 2.25 (t, J=4.7 Hz, 2H), 2.49 (dd, J=12.4 and 4.6 Hz, 1H), 3.04 (m, 4H), 3.19 (dd, J=10.3 Hz, 2H), 3.40 (m, 4H), 5.06 (dd, J=10.3 and 4.5 Hz, 1H), 6.76 (d, J=8.6 Hz, 2H), 6.95 (d, J=8.6 Hz, 2H), 7.27 (m, 5H), 7.59 (t, J=7.8 Hz, 1H), 7.68 (t, J=7.6 Hz, 1H), 8.25 (m, J=8.2 and 7.7 Hz, 4H), 8.39 (d, J=6.1 Hz, 1H), 8.56 (d, J=6.2 Hz, 1H), 8.66 (d, J=6.2 Hz, 1H), 8.83 (d, J=6.1 Hz, 1H), 9.35 (s, 1H), 9.43 (s, 1H).

1-[(S)—N,O-bis-(isoquinolinesulfonyl)-N-methyl-tyrosyl]-4-(phenethyl)-piperazine. Following the general procedure (C), this product was obtained as a yellow solid (yield 25%); m.p.=98–100° C., [α]=+33.2, c=0.84% in CH$_2$Cl$_2$. 1H-NMR (CDCl$_3$) δ: 1.94 (m, 6H), 2.47 (m, 2H), 2.73 (m, 5H), 3.04 (m, 4H), 4.31 (m, 1H), 6.12 (m, 1H), 6.63 (d, J=8.5 Hz, 2H), 6.86 (d, J=8.5 Hz, 2H), 7.22 (m, 5H), 7.62 (dt, J=7.8 Hz, 2H), 8.23 (m, 5H), 8.51 (d, J=6 Hz, 1H), 8.68 (d, J=6.2 Hz, 1H), 8.80 (d, J=6.2 Hz, 1H), 9.32 (s, 1H), 9.41 (s, 1H).

1-[(S)—N,O-bis-(isoquinolinesulfonyl)-N-methyl-tyrosyl]-4-(4-fluorophenyl)-piperazine. Following the general procedure (C), this product was obtained as a yellow solid (yield 38%); m.p.=110–112° C., [α]=−56.6, c=0.45% in CHCl$_3$. 1H-NMR (CDCl$_3$) δ: 2.42 (dd, J=12.6 and 6.2 Hz, 1H), 2.63 (m, 1H), 2.89 (m, 2H), 3.03 (s, 3H), 3.25 (dd, J=12.6 Hz, 2H) 3.55 (m, 4H), 5.12 (dd, J=12 and 6.2 Hz, 1H), 6.80 (m, J=8.5 Hz, 4H), 6.99 (m, J=8.5 Hz, 4H), 7.55 (t, J=7.9 Hz, 1H), 7.71 (t, J=7.9 Hz, 1H), 8.25 (m, J=8 Hz, 4H), 8.42 (d, J=6.3 Hz, 1H), 8.52 (d, J=6.3 Hz, 1H), 8.68 (d, J=6.3 Hz, 1H), 8.81 (d, J=6.3 Hz, 1H), 9.36 (s, 1H), 9.41 (s, 1H).

1-[(S)—N,O-bis-(isoquinolinesulfonyl)-N-methyl-tyrosyl]-4-(4-chlorophenyl)-piperazine. Following the general procedure (C), this product was obtained as a yellow oil (yield 61%); [α]=−43.4, c=0.89% in CHCl$_3$. 1H-NMR (CDCl$_3$) δ: 2.44 (dd, J=12.6 and 6.2 Hz, 1H), 2.92 (m, 4H), 3.00 (s, 3H), 3.57 (m, 4H), 5.11 (dd, J=6.6 and 6.2 Hz, 1H), 6.76 (d, J=8.6 Hz, 4H), 6.95 (d, J=8.6 Hz, 2H), 7.23 (d, J=6.6 Hz, 1H), 7.54 (d, J=8 Hz, 1H), 7.70 (t, J=7.8 Hz, 1H), 8.23 (m, 4H), 8.41 (d, J=6 Hz, 1H), 8.49 (d, J=6 Hz, 1H), 8.67 (d, J=6.2 Hz, 1H), 8.80 (d, J=6 Hz, 1H), 9.35 (s, 1H), 9.41 (s, 1H).

1-[(S)—N,O-bis-(isoquinolinesulfonyl)-N-methyl-tyrosyl]4-(4-iodophenyl)-piperazine. Following the general procedure (C), this product was obtained as a yellow solid (yield 44%); m.p.=95–97° C., [α]=−46.0, c=0.73% in CHCl$_3$. 1H-NMR (CDCl$_3$) δ: 2.42 (dd, J=12.6 and 6.2 Hz, 1H), 2.63 (m, 1H), 2.99 (m, 5H), 3.22 (m, 2H), 3.55(m, 4H), 5.11 (dd, J=13.6 and 6 Hz, 1H), 6.63 (d, J=8.9 Hz, 2H), 6.77 (d, J=8.4 Hz, 2H), 6.96 (d, J=8.4 Hz, 2H), 7.54 (m, J=8.8 and 7.8 Hz, 3H), 7.71 (t, J=7.8 Hz, 1H), 8.24 (m, J=7.6 Hz, 4H), 8.42 (d, J=6.3 Hz, 1H), 8.50 (d, J=6.1 Hz, 1H), 8.68 (d, J=6.1 Hz, 1H), 8.81 (d, J=6.1 Hz, 1H), 9.36 (s, 1H), 9.41 (s, 1H).

1-[(S)—N,O-bis-(isoquinolinesulfonyl)-N-methyl-tyrosyl]-4-(p-tolyl)-piperazine. Following the general procedure, this product was obtained as a foam yellow oil (yield 58%); m.p.=70–72° C., [α]=−41.5, c=0.45% in CHCl$_3$. 1H-NMR (CDCl$_3$) δ: 2.28 (s, 3H), 2.89 (m, 2H), 3.04 (s, 3H), 3.21 (m, 4H), 3.49 (m, 4H), 5.14 (dd, J=12 and 6.2 Hz, 1H), 6.77 (dd, J=6.2 and 3 Hz, 2H), 6.96 (d, J=8.6 Hz, 2H), 7.09 (d, J=8.4 Hz, 2H), 7.49 (t, J=7.8 Hz, 1H), 7.70 (t, J=7.8 Hz, 1H), 8.13 (d, J=7.4 Hz, 2H), 8.17 (t, J=8.8 Hz, 2H), 8.24 (t, J=7.8 Hz, 1H), 8.31 (d, J=7.2 Hz, 1H), 8.41 (d, J=6 Hz, 1H), 8.51 (d, J=6.2 Hz, 1H), 8.68 (d, J=6.2 Hz, 1H), 8.81 (d, J=6 Hz, 1H), 9.35 (s, 1H), 9.40 (s, 1H).

1-[(S)—N,O-bis-(isoquinolinesulfonyl)-N-methyl-tyrosyl]4-(4-methoxyphenyl)-piperazine. Following the general procedure (C), this product was obtained as a white solid (yield 47%); m.p.=85–87° C., [α]=−48.4, c=0.94% in CHCl$_3$. 1H-NMR (CDCl$_3$) δ: 2.48 (dd, J=12 and 4.4 Hz, 2H), 2.83 (m, 4H), 3.16 (s, 3H), 3.52 (m, 4H), 3.77 (s, 3H), 5.11 (dd, J=6.6 and 6.2 Hz, 1H), 6.76 (m, 6H), 6.96 (d, J=8.4 Hz, 2H), 7.51 (d, J=8 Hz, 1H), 7.69 (t, J=8 Hz, 1H), 8.23 (m, 4H), 8.41 (d, J=6.2 Hz, 1H), 8.51 (d, J=6.2 Hz, 1H), 8.67 (d, J=6.2 Hz, 1H), 8.80 (d, J=6.2 Hz, 1H), 9.35 (s, 1H), 9.40 (s, 1H).

1-[(S)—N,O-bis (isoquinolinesulfonyl)-N-methyl-tyrosyl]-4-(4-nitrophenyl)-piperazine. Following the general procedure (C), this product was obtained as a yellow solid (yield 76%); m.p.=77–79° C., [α]=−86, c=1.02% in CHCl$_3$. 1H-NMR (CDCl$_3$) δ: 2.34 (dd, J=14 and 6.2 Hz, 2H), 3.01 (s, 3H), 3.28 (m, 4H), 3.64 (m, 4H), 5.19 (dd, J=13.8 and 6.2 Hz, 1H), 6.78 (d, J=5.2 Hz, 2H), 6.81 (d, J=5.6 Hz, 2H), 6.98 (d, J=8.6 Hz, 2H), 7.59 (t, J=7.8 Hz, 1H), 7.73 (t, J=7.8 Hz, 1H), 8.13 (d, J=7.4 Hz, 2H), 8.17 (d, J=7.4 Hz, 2H), 8.20 (t, J=8.8 Hz, 1H), 8.23 (t, J=8.8 Hz, 1H), 8.44 (d, J=6.2 Hz, 1H), 8.50 (d, J=6.2 Hz, 1H), 8.68 (d, J=6.2 Hz, 1H), 8.80 (d, J=6 Hz, 1H), 9.37 (s, 1H), 9.42 (s, 1H).

1-[(S)—N,O-bis-(isoquinolinesulfonyl)-N-methyl-tyrosyl]-4-(4-cyanophenyl)-piperazine. Following the general procedure (C), this product was obtained as a yellow solid (yield 58%); m.p.=125–127° C., [α]=−67.2, c=0.75% in CHCl$_3$. 1H-NMR (CDCl$_3$) δ: 2.17 (dd, J=12.6 and 6.2 Hz, 2H), 3.00 (s, 3H), 3.17 (m, 4H), 3.69 (m, 4H), 5.11 (dd, J=6.6 and 6 Hz, 1H), 6.80 (m, 4H), 6.97 (d, J=6.8 Hz, 2H), 7.52 (d, J=8.6 Hz, 1H), 7.58 (t, J=7.6 Hz, 1H), 7.72 (t, J=7.8 Hz, 1H), 8.30 (m, 4H), 8.41 (d, J=6 Hz, 1H), 8.49 (d, J=6 Hz, 1H), 8.67 (d, J=6.2 Hz, 1H), 8.81 (d, J=6 Hz, 1H), 9.37 (s, 1H), 9.42 (s, 1H).

1-[(S)—N,O-bis-(isoquinolinesulfonyl)-N-methyl-tyrosyl]-4-(4-acetylphenyl)-piperazine. Following the general procedure (C), this product was obtained as a yellow solid (yield 43%); m.p.=82–84° C., [α]=−56.9, c=1.12% in CHCl$_3$. 1H-NMR (CDCl$_3$) δ: 2.42 (dd, J=12.6 and 6.2 Hz, 1H), 2.53 (s, 3H), 2.90 (m, 1H), 3.02 (s, 3H), 3.21 (m, 5H), 3.63 (m, 3H), 5.14 (dd, J=12 and 6.2 Hz, 1H), 6.79 (t, J=8.5, 4H), 6.95 (d, J=8.5 Hz, 2H), 7.52 (t, J=7.8 Hz, 1H), 7.71 (t, J=7.8 Hz, 1H), 7.89 (d, J=8.9 Hz, 2H), 8.24 (m, J=7.4 Hz, 4H), 8.41 (d, J=6.1 Hz, 1H), 8.49 (d, J=6.2 Hz, 1H), 8.68 (d, J=6.2 Hz, 1H), 8.79 (d, J=6.1 Hz, 1H), 9.35 (s, 1H), 9.39 (s, 1H).

Preparation of 1-[(S)—N,O-bis-(isoquinolinesulfonyl)-N-methyl-tyrosyl]-4-(4-fluorobenzyl)-piperazine. Following the general procedure (C), this product was obtained as a yellow solid (yield 10%); m.p.=103–105° C., [α]=−21.5, c=0.72% in CHCl$_3$. 1H-NMR (CDCl$_3$) δ: 1.95 (m, 1H), 2.24 (m, 3H), 2.49 (dd, J=12.4 and 4.6 Hz, 1H), 3.04 (m, 4H), 3.14 (m, 2H), 3.38 (m, 4H), 5.06 (dd, J=10.3 and 4.5 Hz, 1H), 6.78 (d, J=8.4 Hz, 2H), 6.99 (m, J=8.4 Hz, 4H), 7.22 (m, 2H), 7.66 (dt, J=7.8 Hz, 2H), 8.25 (m, 4H), 8.39 (d, J=6.2 Hz, 1H), 8.56 (d, J=6 Hz, 1H), 8.66 (d, J=6.3 Hz, 1H), 8.83 (d, J=6.2 Hz, 1H), 9.36 (s, 1H), 9.44 (s, 1H).

1-[(S)—N,O-bis-(isoquinolinesulfonyl)-N-methyl-tyrosyl]-4-(4-fluorobenzoyl)-piperazine. Following the general procedure (C), this product was obtained as a yellow solid (yield 18%); m.p.=124–126° C., [α]=−37.8, c=0.82% in CH$_2$Cl$_2$. 1H-NMR (CDCl$_3$) δ: 2.49 (m, 1H), 2.79 (m, 1H), 3.03 (s, 3H), 3.28 (m, 6H), 3.57 (m, 2H), 5.07 (dd, J=10.9 and 4.3 Hz, 1H), 6.79 (m, J=8.4 Hz, 2H), 6.97 (d, J=8.5 Hz, 2H), 7.12 (t, J=8.6 Hz, 2H), 7.44 (m, 2H), 7.72 (t, J=7.9 Hz, 2H), 8.31 (m, 5H), 8.54 (d, J=5.9 Hz, 1H), 8.68 (d, J=6 Hz, 1H), 8.84 (d, J=6 Hz, 1H), 9.38 (s, 1H), 9.45 (s, 1H).

1-[(S)—N,O-bis-(isoquinolinesulfonyl)-N-methyl-tyrosyl]4-(4-nitrobenzyl)-piperazine. Following the general procedure (C), this product was obtained as a yellow solid (yield 40%); m.p.=145–147° C., [α]=−28.4, c=0.37% in CHCl$_3$. 1H-NMR (CDCl$_3$) δ: 1.95 (m, 1H), 2.27 (m, 3H), 2.49 (dd, J=12.4 and 4.6 Hz, 1H), 2.02 (m, 4H), 3.21 (dd, J=10.3 Hz, 2H), 3.49 (m, 4H), 5.12 (dd, J=10.3 and 4.5 Hz, 1H), 6.82 (d, J=8.4 Hz, 2H), 6.97 (d, J=8.6 Hz, 2H), 7.48 (d, J=8.4 Hz, 2H), 7.68 (m, J=8.3 Hz, 2H), 8.18 (d, J=8.6 Hz, 3H), 8.30 (m, J=7.5 Hz, 3H), 8.40 (d, J=6 Hz, 1H), 8.55 (d, J=6.2 Hz, 1H), 8.67 (d, J=6 Hz, 1H), 8.83 (d, J=6.3 Hz, 1H), 9.37 (s, 1H), 9.45 (s, 1H).

1-[(S)—N,O-bis-(isoquinolinesulfonyl)-N-methyl-tyrosyl]4-(2-fluorophenyl)-piperazine. Following the general procedure (C), this product was obtained as a yellow solid (yield 76%); m.p.=133–135° C., [α]=−58.4, c=0.44% in CHCl$_3$. 1H-NMR (CDCl$_3$) δ: 2.49 (m, 1H), 3.06 (s, 3H), 3.22 (m, 4H), 3.63 (m, 4H), 5.11 (dd, J=13.6 and 6 Hz, 1H), 6.79 (m, 4H), 7.00 (m, 4H), 7.57 (t, J=8.2 Hz, 1H), 7.70 (t, J=7.8 Hz, 1H), 8.25 (m, 4H), 8.41 (d, J=6.2 Hz, 1H), 8.52 (d, J=6.2 Hz, 1H), 8.67 (d, J=6.2 Hz, 1H), 8.81 (d, J=6.2 Hz, 1H), 9.36 (s, 1H), 9.42 (s, 1H).

1-[(S)—N,O-bis-(isoquinolinesulfonyl)-N-methyl-tyrosyl]4-(2-chlorophenyl)-piperazine. Following the general procedure (C), this product was obtained as a yellow solid (yield 58%); m.p.=84–86° C., [α]=−39.2, c=0.92% in CHCl$_3$. 1H-NMR (CDCl$_3$) δ: 2.48 (m, J=12.4 and 4.6 Hz, 2H), 2.83 (m, 2H), 3.07 (s, 3H), 3.23 (t, J=10.4 Hz, 2H), 3.58 (m, 4H), 5.12 (dd, J=10.3 and 4.5 Hz, 1H), 6.77 (d, J=8.6 Hz, 2H), 6.97 (m, J=8.6 Hz, 4H), 7.23 (d, J=7.8 Hz, 1H), 7.38 (d, J=8.8 Hz, 1H), 7.58 (t, J=7.8 Hz, 1H), 7.71 (t, J=7.7 Hz, 1H), 8.25 (m, J=8.3 and 7.4 Hz, 4H), 8.42 (d, J=6.2 Hz, 1H), 8.54 (d, J=6 Hz, 1H), 8.68 (d, J=5.9 Hz, 1H), 8.82 (d, J=6.2 Hz, 1H), 9.37 (s, 1H), 9.43 (s, 1H).

1-[(S)—N,O-bis-(isoquinolinesulfonyl)-N-methyl-tyrosyl]-4-(o-tolyl)-piperazine. Following the general procedure (C), this product was obtained as a yellow solid (yield 58%); m.p.=84–86° C., [α]=−39.2, c=0.92% in CHCl$_3$. 1H-NMR (CDCl$_3$) δ: 2.28 (s, 3H), 2.35 (m, 1H), 2.49 (dd, J=12.4 and 4.6 Hz, 1H), 2.68 (m, 2H), 3.06 (s, 3H), 3.30 (m, 2H), 3.58 (m, 4H), 5.12 (dd, J=10.3 and 4.5 Hz, 1H), 6.81 (t, J=9.0 and 8.4 Hz, 3H), 7.02 (m, J=8.9 and 8.5 Hz, 3H), 7.18 (t, J=7.4 Hz, 2H), 7.56 (t, J=7.7 Hz, 1H), 7.72 (t, J=7.7 Hz, 1H), 8.27 (m, J=8.4 and 6.1 Hz, 4H), 8.42 (d, J=6.2 Hz, 1H), 8.54 (d, J=6 Hz, 1H), 8.68 (d, J=6.2 Hz, 1H), 8.82 (d, J=6 Hz, 1H), 9.37 (s, 1H), 9.43 (s, 1H).

1-[(S)—N,O-bis-(isoquinolinesulfonyl)-N-methyl-tyrosyl]4-(2-methoxyphenyl)-piperazine. Following the general procedure(C), this product was obtained as a yellow solid (yield 10%); m.p.=85–87° C., [α]=−29.8, c=0.45% in CHCl$_3$. 1H-NMR (CDCl$_3$) δ: 2.51 (dd, J=12.6 and 6.2 Hz, 1H), 2.62 (m, 1H), 2.87 (m, 2H), 3.07 (s, 3H), 3.22 (m, 2H), 3.56 (m, 4H), 3.87 (s, 3H), 5.15 (dd, J=13.6 and 6 Hz, 1H), 6.76 (d, J=8.6 Hz, 2H), 6.97 (m, J=7.9 Hz, 4H), 7.30 (m, 1H), 7.63 (m, 3H), 8.11 (d, J=8.1 Hz, 1H), 8.27 (m, J=7.3 Hz, 3H), 8.44 (m, 1H), 8.54 (d, J=6 Hz, 1H), 8.75 (m, 2H), 9.40 (m, 2H).

1-[(S)—N,O-bis-(isoquinolinesulfonyl)-N-methyl-tyrosyl]-4-(3-chlorophenyl)-piperazine. Following the general procedure (C), this product was obtained as a yellow solid (yield 67%); m.p.=138–140° C., [α]=−58.8, c=0.6% in CHCl$_3$. 1H-NMR (CDCl$_3$) δ: 2.42 (m, 2H), 2.99 (s, 3H), 3.22 (m, 4H), 3.59 (m, 4H), 5.12 (dd, J=12 and 6.2 Hz, 1H), 6.79 (m, 4H), 6.89 (m, 3H), 7.21 (t, J=8 Hz, 1H), 7.54 (t, J=8 Hz, 1H), 7.72 (t, J=8 Hz, 1H), 8.26 (m, 4H), 8.42 (d, J=6.2 Hz, 1H), 8.51 (d, J=6.2 Hz, 1H), 8.68 (d, J=6.2 Hz, 1H), 8.81 (d, J=6.2 Hz, 1H), 9.37 (s, 1H), 9.42 (s, 1H).

1-[(S)—N,O-bis-(isoquinolinesulfonyl)-N-methyl-tyrosyl]-4-(3-trifluoromethylphenyl)-piperazine. Following the general procedure (C), this product was obtained as a yellow solid (yield 20%); m.p.=81–83° C., [α]=−61.5, c=0.4% in CHCl$_3$. 1H-NMR (CDCl$_3$) δ: 2.48 (dd, J=12 and 4.4 Hz, 1H), 2.75 (m, 1H), 2.93 (m, 5H), 3.30 (m, 2H), 3.62 (m, 4H), 5.11 (dd, J=6.6 and 6.2 Hz, 1H), 6.78 (d, J=8.6 Hz, 2H), 6.99 (m, J=8.6 Hz, 4H), 7.15 (d, J=7.8 Hz, 1H), 7.40 (t, J=8.8 Hz, 1H), 7.55 (t, J=7.8 Hz, 1H), 7.72 (t, J=7.7 Hz, 1H), 8.23 (m, 4H), 8.43 (d, J=6 Hz, 1H), 8.51 (d, J=6.3 Hz, 1H), 8.68 (d, J=6.4 Hz 1H), 8.80 (d, J=6 Hz 1H), 9.36 (s, 1H), 9.41 (s, 1H).

1-[(S)—N,O-bis-(isoquinolinesulfonyl)-N-methyl-tyrosyl]4-(2,3-dimethylphenyl)-piperazine. Following the general procedure (C), this product was obtained as a brown solid (yield 21%); m.p.=174–176° C., [α]=−17.5, c=1.91% in CH$_2$Cl$_2$. 1H-NMR (CDCl$_3$) δ: 2.19 (s, 3H), 2.27 (s, 3H), 2.49 (dd, J=12.4 and 4.6 Hz, 1H), 2.68 (m, 3H), 3.06 (s, 3H), 3.25 (m, 2H), 3.58 (m, 4H), 5.12 (dd, J=10.3 and 4.5 Hz, 1H), 6.76 (m, J=8.7 Hz, 3H), 7.03 (m, J=8.7 Hz, 4H), 7.56 (t, J=7.7 Hz, 1H), 7.71 (t, J=7.7 Hz, 1H), 8.26 (m, J=7 Hz, 4H), 8.44 (d, J=6.1 Hz, 1H), 8.54 (d, J=6.2 Hz, 1H), 8.68 (d, J=6.2 Hz, 1H), 8.82 (d, J=6 Hz, 1H), 9.36 (s, 1H), 9.42 (s, 1H).

1-[(S)—N,O-bis-(isoquinolinesulfonyl)-N-methyl-tyrosyl]-4-(3,4-dichlorophenyl)-piperazine. Following the general procedure (C), this product was obtained as a yellow solid (yield 64%); m.p.=130–132° C., [α]=−73.4, c=0.44% in CHCl$_3$. 1H-NMR (CDCl$_3$) δ: 2.96 (m, 2H), 3.02 (s, 3H), 3.41 (m, 4H), 3.63 (m, 4H), 5.16 (dd, J=13.6 and 6 Hz, 1H), 6.80 (m, 4H), 6.94 (t, J=8.4 Hz, 3H), 7.57 (t, J=8 Hz, 1H), 7.72 (t, J=8 Hz, 1H), 8.22 (m, 4H), 8.44 (d, J=6 Hz, 1H), 8.52 (d, J=6 Hz, 1H), 8.66 (d, J=6 Hz, 1H), 8.81 (d, J=6 Hz, 1H), 9.37 (s, 1H), 9.42 (s, 1H).

1-[(S)—N,O-bis-(isoquinolinesulfonyl)-N-methyl-tyrosyl]-4-(pyridin-2-yl)-piperazine. Following the general procedure (C), this product was obtained as a yellow solid (yield 48%); m.p.=183–185° C., [α]=−55.8, c=0.41% in CH$_2$Cl$_2$. 1H-NMR (CDCl$_3$) δ: 2.46 (dd, J=12.7 and 4.3 Hz, 1H), 2.91 (m, 1H), 3.05 (s, 3H), 3.21 (m, J=10.6 Hz, 3H), 3.42 (m, 3H), 5.09 (dd, J=10.4 and 4.4 Hz, 1H), 6.60 (d, J=8.6 Hz, 1H), 6.70 (m, J=8.4 Hz, 3H), 6.96 (d, J=8.4 Hz, 2H), 7.53 (m, 2H), 7.70 (t, J=7.8 Hz, 1H), 8.12 (d, J=7.3 Hz, 1H), 8.22 (m, 3H), 8.30 (d, J=7.3 Hz, 1H), 8.41 (d, J=6.2 Hz, 1H), 8.51 (d, J=6.2 Hz, 1H), 8.67 (d, J=6.3 Hz, 1H), 8.80 (d, J=6.1 Hz, 1H), 9.35 (s, 1H), 9.40 (s, 1H).

1-[(S)—N,O-bis-(isoquinolinesulfonyl)-N-methyl-tyrosyl]4-(pyrimidin-2-yl)-piperazine. Following the general procedure (C), this product was obtained as a yellow solid (yield 32%); m.p.=187–189° C., [α]=−54.6, c=0.76% in $CH_2Cl_2$. 1H-NMR ($CDCl_3$) δ: 2.46 (dd, J=12.7 and 4.3 Hz, 1H), 3.00 (m, 1H), 3.06 (s, 3H), 3.41 (m, J=10.4 Hz, 6H), 3.80 (m, 2H), 5.09 (dd, J=10.4 and 4.4 Hz, 1H), 6.56 (t, J=8.6 Hz, 1H), 6.74 (d, J=8.5 Hz, 2H), 6.96 (d, J=8.5 Hz, 2H), 7.57 (t, J=7.8 Hz, 1H), 7.70 (t, J=7.8 Hz, 1H), 8.21 (m, J=7.6 Hz, 4H), 8.33 (m, 2H), 8.40 (d, J=6.3 Hz, 1H), 8.52 (d, J=6.1 Hz, 1H), 8.67 (d, J=6 Hz, 1H), 8.82 (d, J=6 Hz, 1H), 9.35 (s, 1H), 9.41 (s, 1H).

1-[(S)—N,O-bis-(isoquinolinesulfonyl)-N-methyl-tyrosyl]4-(benzyl)-piperidine. Following the general procedure (C), this product was obtained as a yellow solid (yield 35%); m.p.=131–133° C., [α]=−24, c=0.42% in $CH_2Cl_2$. 1H-NMR ($CDCl_3$) δ: 1.50 (m, 2H), 2.39 (m, 6H), 2.70 (m, 1H), 3.04 (s, 3H), 3.25 (m, 2H), 3.80 (m, 1H), 4.40 (m, 1H), 5.10 (m, 1H), 6.73 (m, 1H), 6.88 (d, J=8.6 Hz, 2H), 7.05 (m, 3H), 7.24 (m, 3H), 7.68 (m, 2H), 8.26 (m, 4H), 8.41 (d, J=6.1 Hz, 1H), 8.56 (d, J=6.2 Hz, 1H), 8.68 (d, J=6.2 Hz, 1H), 8.82 (d, J=6 Hz, 1H), 9.35 (s, 1H), 9.43 (s, 1H).

1-[(S)—N,O-bis-(isoquinolinesulfonyl)tyrosyl]-4-(4-fluorophenyl)-piperazine. Following the general procedure (C), this product was obtained as a yellow solid (yield 50%); m.p.=145–147° C., [α]=+47.7, c=0.62% in $CH_2Cl_2$. 1H-NMR ($CDCl_3$) δ: 2.22 (m, 2H), 2.50 (m, 4H), 3.06 (m, 3H), 3.25 (m, 1H), 4.35 (m, 1H) 5.99 (d, 1H), 6.65 (d, J=8.4 Hz, 2H), 6.78 (m, 2H), 6.88 (d, J=8.5 Hz, 2H), 6.99 (t, J=8.5 Hz, 2H), 7.58 (m, 2H), 8.16 (t, J=8 Hz, 2H), 8.27 (t, J=6.5 Hz, 3H), 8.51 (d, J=6.3 Hz, 1H), 8.70 (d, J=6.3 Hz, 1H), 8.82 (d, J=6 Hz, 1H), 9.30 (s, 1H), 9.41 (s, 1H).

1-[(S)—N,O-bis-(isoquinolinesulfonyl)-tyrosyl]4-(o-tolyl)-piperazine. Following the general procedure (C), this product was obtained as a yellow solid (yield 88%); m.p.=132–134° C., [α]=+80.3, c=1% in $CH_2Cl_2$. 1H-NMR ($CDCl_3$) δ: 2.24 (s, 3H) 2.36 (m, 3H), 2.54 (m, 1H), 2.80 (d, J=7.2 Hz, 2H), 2.93 (m, 1H), 3.06 (m, 1H), 3.25 (m, 2H), 4.35 (m, J=7.5 Hz, 1H), 6.09 (d, J=9.1 Hz, 1H), 6.4 (d, J=8.3 Hz, 2H), 6.85 (m, J=8.6 and 7.8 Hz, 3H), 7.03 (t, J=7.4 Hz, 1H), 7.18 (m, 2H), 7.55 (t, J=7.9 Hz, 1H), 7.63 (t, J=7.7 Hz, 1H), 8.24 (m, J=7.5 Hz, 5H), 8.52 (d, J=6 Hz, 1H), 8.69 (d, J=6.2 Hz, 1H), 8.82 (d, J=6 Hz, 2H), 9.33 (s, 1H), 9.41 (s, 1H).

Preparation of 1-[(S)—N,O-bis (isoquinolinesulfonyl)-N-methyl-tyrosyl]-4-(4-amino-phenyl)-piperazine. Following the general procedure (C), this product was obtained as a yellow solid (yield 45%); m.p.=80–82° C., [α]=−48,4 c=0.90% in $CHCl_3$. 1H-NMR ($CDCl_3$) δ: 2.48 (m, 2H), 2.83 (m, 4H), 3.16 (s, 3H), 3.52 (m, 4H), 4.00 (m, 2H), 5.11 (dd, J=6.6 and 6.2 Hz, 1H), 6.28 (d, J=8.3 Hz, 2H), 6.34 (d, J=8.3 Hz, 2H), 6.76 (d, J=8.4 Hz, 2H), 6.96 (d, J=8.4 Hz, 2H), 7.51 (d, J=8 Hz, 1H), 7.69 (t, J=8 Hz, 1H), 8.23 (m, 4H), 8.41 (d, J=6.2 Hz, 1H), 8.51 (d, J=6.2 Hz, 1H), 8.67 (d, J=6.2 Hz, 1H), 8.80 (d, J=6.2 Hz, 1H), 9.35 (s, 1H), 9.40 (s, 1H).

1,2,3,4-Tetrahydro-2-[(S)—N,O-bis(isoquinolinesulfonyl)-tyrosyl]-1,4-pyrazino[1,2-a]indole. Following the general procedure C this product was obtained. m.p. 83–85° C.; [a]=+8.0, c=0.5% in $CHCl_3$; 1H-NMR (CDCl3) d 2.86 (m, 5H), 3.45 (m, 2H), 3.64 m, 1H), 4.28 (m, 2H), 6.02 (d, J=9.4 Hz, 1H), 6.1 (t, J=14.6 Hz, 1H), 6.72 (m, 3H), 6.94 (m, 2H), 7.22 (m, 2H), 7.37 (m, 2H), 7.61 (t, J=8.2 Hz, 1H), 8.06 (m, 5H), 8.46 (d, J=6 Hz, 1H), 8.69 (m, 1H), 9.08 (s, 1H), 9.35 (s, 1H).

1,2,3,4-Tetrahydro-2-[(S)—N,O-bis(isoquinolinesulfonyl)-N-methyl-tyrosyl]-1,4-pyrazino[1,2-a]indole. Following the general procedure C this product was obtained. m.p. 110–112° C.; [a]=−4.5, c=0.58% in CHCl3; 1H-NMR (CDCl3): d 2.53 (m, 1H), 3.02 (s, 3H), 3.12 (m, 1H), 3.59 (m, 5H), 4.57 (dd, J=8.8 and 6 Hz, 1H), 4.86 (d, 8.8 Hz, 1H), 5.12 (m, 1H), 6.28 (d, J=9.0 Hz, 1H), 6.68 (t, J=6.8 Hz, 2H), 6.96 (t, J=6.8 Hz, 2H), 7.24 (m, 3H), 7.39 (q, J=7.2 Hz, 2H), 7.56 (t, J=7.8 Hz, 1H), 8.11 (m, 5H), 8.46 (d, J=6.2 Hz, 1H), 8.77 (t, J=4.2 Hz, 1H), 9.16 (s, 1H), 9.28 (s, 1H).

1,2,3,4-Tetrahydro-2-[(S)—N,O-bis(isoquinolinesulfonyl)-N-methyl-tyrosyl]-8-fluoro-1,4-pyrazino[1,2-a]indole. Following the general procedure C this product was obtained. m.p. 105–107° C.; [a]=−37, c=0.58% in CHCl3; 1H-NMR (CDCl3): d 2.53 (m, 1H), 3.02 (s, 3H), 3.24 (m, 1H), 3.69 (m, 5H), 4.64 (dd, J=9.2 and 6.2 Hz, 1H), 4.88 (d, 8.8 Hz, 1H), 5.12 (m, 1H), 6.28 (d, J=9.0 Hz, 1H), 6.68 (t, J=9.0 Hz, 2H), 6.96 (m, 3H), 7.45 (t, J=7.8 Hz, 1H), 7.58 (t, J=7.8 Hz, 1H), 7.57 (t, J=7.8 Hz, 1H), 8.16 (m, 5H), 8.46 (d, J=6.0 Hz, 1H), 8.64 (d, J=4.2 Hz, 1H), 8.80 (t, J=6.4 Hz, 1H), 9.20 (s, 1H), 9.30 (s, 1H).

Changes in plasma membrane permeability. ATP-dependent increases in plasma membrane permeability were measured with the extracellular fluorescent tracer ethidium bromide (Molecular Probes, Inc., Eugene, Oreg.). For ethidium bromide uptake cells were incubated in a thermostat-controlled fluorometer cuvette (37° C.) for 20 min in the dark at a concentration of $10^6$ cells/ml in the presence of 20 mM ethidium bromide and challenged with 1 mM ATP. Cell suspension was incubated with KN62 or synthesized compounds (25 nM–5000 nM) for 5 min at 37° C. before fluorimetric analysis in a stirred cuvette at 37° C. Fluorescence changes were monitored at the wavelength pair 360/580 nm. After several washings to remove the extracellular dye, cells were analyzed with an inverted fluorescence microscope (Olympus IMT-2, Olympus Optical Co. Ltd., Tokyo, Japan). All experiments were repeated three times.

$Ca^{2+}$ measurements. Changes in $Ca^{2+}$ were measured with the fluorescent indicator fura-2/AM (Molecular Probes, Inc., Eugene, Oreg.) as described previously.[32] Briefly, cells were loaded with 4 mM of fura-2/AM and incubated in a thermostat-controlled (37° C.) and magnetically stirred fluorometer cuvette (model LS50, Perkin-Elmer Ltd., Beaconsfield, UK). Intracellular $Ca^{2+}$ concentration was determined with the 340/380 excitation ratio at an emission wavelength of 500 nM. All experiments were repeated three times.

Cytokine release. IL-1β release was measured in macrophage monolayers primed for two h with bacterial endotoxin (lipopolysaccharide, LPS) at the concentration of 10 μg/ml, and the stimulated with 3 mM ATP for 30 min. Inhibitors, when used, were added 5 min prior to ATP. Supernatants were centrifuged for 5 min at 900 g to remove floating cells and were assayed for IL-1β content by ELISA (R&D Systems, Minneapolis, Minn., USA).

TABLE I

| COMPOUND | $P2X_7$ Antagonist Activity $IC_{50}$ (nM) |
| --- | --- |
| KN62 | 51 |
| 1-[(S)-N,O-bis-(isoquinolinesulfonyl)-N-methyl-tyrosyl]-4-(4-nitrophenyl)-piperazine | 5.76 |

TABLE I-continued

| COMPOUND | P2X$_7$ Antagonist Activity IC$_{50}$ (nM) |
|---|---|
| 1-[(S)-N,O-bis-(isoquinolinesulfonyl)-N-methyl-tyrosyl]-4-(4-aminophenyl)-piperazine | 101 |
| 1-[(S)-N,O-bis-(isoquinolinesulfonyl)-N-methyl-tyrosyl]-4-(4-chlorophenyl)-piperazine] | 104.7 |
| 1-[(S)-N,O-bis-(isoquinolinesulfonyl)-N-methyl-tyrosyl]-4-(4-methoxy-phenyl)-piperazine | 131.8 |
| 1-[(S)-N,O-bis-(isoquinolinesulfonyl)-N-methyl-tyrosyl]-4-benzylpiperazine | 21 |
| 1-[(S)-N,O-bis-(isoquinolinesulfonyl)-N-methyl-tyrosyl]-4-(4-acetylphenyl)-piperazine] | 70.79 |
| 1-[(S)-N,O-bis-(isoquinolinesulfonyl)-N-methyl-tyrosyl]-4-(4-fluorophenyl)-piperazine | 1.33 |
| 1-[(S)-N,O-bis-(isoquinolinesulfonyl)-N-methyl-tyrosyl]-4-(4-iodophenyl)-piperazine] | 175.8 |
| 1-[(S)-N,O-bis-(isoquinolinesulfonyl)-N-methyl-tyrosyl]-4-(p-tolyl)-piperazine | 13.48 |
| 1-[(S)-N,O-bis-(isoquinolinesulfonyl)-N-methyl-tyrosyl]-4-(2-chlorophenyl)-piperazine | 15.84 |
| 1-[(S)-N,O-bis-(isoquinolinesulfonyl)-N-methyl-tyrosyl]-4-(2-methoxy-phenyl)-piperazine | 84.13 |
| 1-[(S)-N,O-bis-(isoquinolinesulfonyl)-N-methyl-tyrosyl]-4-(4-cyanophenyl)-piperazine] | 97.74 |
| 1-[(S)-N,O-bis-(isoquinolinesulfonyl)-N-methyl-tyrosyl]-4-(3-trifluoromethyl-phenyl)-piperazine | 31.15 |
| 1-[(S)-N,O-bis-(isoquinolinesulfonyl)-N-methyl-tyrosyl]-4-(4-nitrobenzyl)-piperazine] | 12.3 |
| 1-[(S)-N,O-bis-(isoquinolinesulfonyl)-N-methyl-tyrosyl]-4-(2-fluorophenyl)-piperazine] | 18.53 |
| 1-[(S)-N,O-bis-(isoquinolinesulfonyl)-N-methyl-tyrosyl]-4-(4-fluorobenzyl)-piperazine] | 5.8 |
| 1-[(S)-N,O-bis-(isoquinolinesulfonyl)-N-methyl-tyrosyl]-4-(3,4-dichloro-phenyl)-piperazine | 33.89 |
| 1-[(S)-N,O-bis-(isoquinolinesulfonyl)-N-methyl-tyrosyl]-4-(3-chlorophenyl)-piperazine | 14.13 |
| 1-[(S)-N,O-bis-(isoquinolinesulfonyl)-N-methyl-tyrosyl]-4-o-tolyl-piperazine | 15.1 |
| 1-[(S)-N,O-bis-(isoquinolinesulfonyl)tyrosyl]-4-(4-fluorophenyl)-piperazine | 6.02 |
| 1-[(S)-N,O-bis-(isoquinolinesulfonyl)-N-methyl-tyrosyl]-4-(pyridin-2-yl)-piperazine | 170 |
| 1-[(S)-N,O-bis-(isoquinolinesulfonyl)-N-methyl-tyrosyl]-4-(pyrimidin-2-yl)-piperazine | 79.8 |
| 1-[(S)-N,O-bis-(isoquinolinesulfonyl)-N-methyl-tyrosyl]-4-(4-fluorobenzoyl)-piperazine] | 380.2 |
| 1-[(S)-N,O-bis-(isoquinolinesulfonyl)-N-methyl-tyrosyl]-4-benzylpiperidine | 65.31 |
| 1-[(S)-N,O-bis-(isoquinolinesulfonyl)-N-methyl-tyrosyl]-4-phenethyl-piperazine | 599.8 |
| 1-[(S)-N,O-bis-(3-pyridinesulfonyl)-N-methyl-tyrosyl]-4-phenyl-piperazine | 955 |
| 1-[(S)-N,O-bis-(3-pyridinesulfonyl)-N-methyl-tyrosyl]-4-(2-methylphenyl)-piperazine | 9120 |
| 1-[(S)-N,O-bis-(isoquinolinesulfonyl)tyrosyl]-4-(o-tolyl)-piperazine | 28.84 |
| 1-[(S)-N,O-bis-(isoquinolinesulfonyl)-N-methyl-tyrosyl]-4-(2,3-dimethylphenyl)-piperazine | 1122 |

What is claimed is:

1. A compound of the formula wherein
$R_1$ is methyl substituted at the ortho-position;
$R_2$ is hydrogen;
$R_3$ and $R_8$ are each nitrogen;
$R_4$, $R_5$, $R_6$, and $R_7$, are each CH;
$R_9$ is methyl;
$R_{10}$ is $(CH_2)_n$ where n is 0;
$R_{11}$ and $R_{12}$ are each CH;
$X_1$ and $X_2$ are each tritium; and
$X_3$ is nitrogen.

2. A compound of the formula wherein
wherein $R_1$ and $R_2$ are independently hydrogen, C1–C4 alkyl, C1–C4 substituted alkyl, C1–C4 alkoxy, C1–C4 substituted alkoxy, C1–C4 acyl, halogen, cyano, nitro, amino, alkylamino, or dialkylamino;
$R_3$, $R_5$, $R_6$, and $R_8$ are independently CH;
$R_4$ and $R_7$ are independently nitrogen;
$R_9$ is hydrogen or methyl;
$R_{10}$ is C=O or $(CH_2)_n$ where n is 0 or 1;
$R_{11}$ and $R_{12}$ are independently nitrogen or CH; $X_1$ and $X_2$ are independently hydrogen, deuterium, tritium or halogen; and $X_3$ is nitrogen;
with the proviso that when n is 0, and $R_{11}$ and $R_{12}$ are CH, either $R_1$ or $R_2$ is C1–C4 alkyl, C1–C4 alkoxy, C1–C4 acyl, halogen, cyano, nitro or amino.

3. A compound of the formula wherein;
R₁ and R₂ are independently hydrogen, C1–C4 alkyl, C1–C4 alkoxy, C1–C4 acyl, halogen, cyano, nitro, amino, alkylamino, or dialkylamino; $R_9$ is hydrogen or methyl; $X_1$ and $X_2$ are independently hydrogen, deuterium, tritium, or halogen; and $X_3$ is nitrogen.

4. The pharmaceutically acceptable salts of a compound of claim 3.

5. A compounds of the formula wherein
R₁ and R₂ are independently hydrogen, C1–C4 alkyl, C1–C4 alkoxy, halogen, cyano, nitro, or amino;
R₃, R₅, R₆, and R₈ are independently CH, and where R₄ and R₇ are independently nitrogen; and
n is 0 or 1;
with the proviso that when n is 0 either R₁ or R₂ is not hydrogen.

6. A compound selected from the group of tyrosyl piperazine derivatives consisting of:
   a. (S)—N-tert-butyloxycarbonyl-N-methyl-tyrosyl]-4-(4-nitrophenyl)-piperazine;
   b. 1-[(S)—N-tert-butyloxycarbonyl-N-methyl-tyrosyl]-4-(p-tolyl)-piperazine;
   c. 1-[(S)—N-tert-butyloxycarbonyl-N-methyl-tyrosyl]-4-(2-chlorophenyl)-piperazine;
   d. 1-[(S)—N-tert-butyloxycarbonyl-N-methyl-tyrosyl]-4-(4-fluorophenyl)-piperazine;
   e. 1-[(S)—N-tert-butyloxycarbonyl-N-methyl-tyrosyl]-4-(3,4-dichlorophenyl)-piperazine;
   f. 1-[(S)—N-tert-butyloxycarbonyl-N-methyl-tyrosyl]-4-(4-cyanophenyl)-piperazine;
   g. 1-[(S)—N-tert-butyloxycarbonyl-N-methyl-tyrosyl]-4-(4-chlorophenyl)-piperazine;
   h. 1-[(S)—N-tert-butyloxycarbonyl-N-methyl-tyrosyl]-4-(4-methoxyphenyl)-piperazine;
   i. 1-[(S)—N-tert-butyloxycarbonyl-N-methyl-tyrosyl]-4-benzyl-piperazine;
   j. 1-[(S)—N-tert-butyloxycarbonyl-N-methyl-tyrosyl]-4-(4-iodophenyl)-piperazine;
   k. 1-[(S)—N-tert-butyloxycarbonyl-N-methyl-tyrosyl]-4-(4-acetylphenyl)-piperazine;
   l. 1-[(S)—N-tert-butyloxycarbonyl-N-methyl-tyrosyl]-4-(4-fluorobenzyl)-piperazine;
   m. 1-[(S)—N-tert-butyloxycarbonyl-N-methyl-tyrosyl]-4-(4-fluorobenzoyll)-piperazine;
   n. 1-[(S)—N-tert-butyloxycarbonyl-N-methyl-tyrosyl]-4-(4-nitrobenzyl)-piperazine;
   o. 1-[(S)—N-tert-butyloxycarbonyl-N-methyl-tyrosyl]-4-(2-fluorophenyl)-piperazine;
   p. 1-[(S)—N-tert-butyloxycarbonyl-N-methyl-tyrosyl]-4-(o-tolyl)-piperazine;
   q. 1-[(S)—N-tert-butyloxycarbonyl-N-methyl-tyrosyl]-4-(2-methoxyphenyl)-piperazine;
   r. 1-[(S)—N-tert-butyloxycarbonyl-N-methyl-tyrosyl]-4-(3-chlorophenyl)-piperazine;
   s. 1-[(S)—N-tert-butyloxycarbonyl-N-methyl-tyrosyl]-4-(3-trifluoromethylphenyl)-piperazine;
   t. 1-[(S)—N-tert-butyloxycarbonyl-N-methyl-tyrosyl]-4-(2,3-dimethylphenyl)-piperazine;
   u. 1-[(S)—N-tert-butyloxycarbonyl-N-methyl-tyrosyl]-4-(pyridin-2-yl)-piperazine;
   v. 1-[(S)—N-tert-butyloxycarbonyl-N-methyl-tyrosyl]-4-(pyrimidin-2-yl)-piperazine;
   w. 1-[(S)—N-tert-butyloxycarbonyl-N-methyl-tyrosyl]-4-benzyl-piperidine;
   x. 1-[(S)—N-tert-butyloxycarbonyl-tyrosyl]-4-(4-fluorophenyl)-piperazine;
   y. 1-[(S)—N-tert-butyloxycarbonyl-tyrosyl]-4-(o-tolyl)-piperazine;
   z. 1-[(S)—N-tert-butyloxycarbonyl-N-methyl-tyrosyl]-4-(4-aminophenyl)-piperazine; and
   aa. 1-[(S)—N-tert-butyloxycarbonyl-N-methyl-tyrosyl]-4-(4-bromo-2-methylphenyl)-piperazine.

7. A compound selected from the group of tyrosyl piperazine derivatives consisting of:
   a. 1-[(S)—O-isoquinolinesulfonyl-N-tert-butyloxycarbonyl-N-methyl-tyrosyl]-4-(4-nitrophenyl)-piperazine];
   b. 1-[(S)—O-isoquinolinesulfonyl-N-tert-butyloxycarbonyl-N-methyl-tyrosyl]-4-(p-tolyl)-piperazine];
   c. 1-[(S)—O-isoquinolinesulfonyl-N-tert-butyloxycarbonyl-N-methyl-tyrosyl]-4-(2-chlorophenyl)-piperazine];
   d. 1-[(S)—O-isoquinolinesulfonyl-N-tert-butyloxycarbonyl-N-methyl-tyrosyl]-4-(4-fluorophenyl)-piperazine];
   e. 1-[(S)—O-isoquinolinesulfonyl-N-tert-butyloxycarbonyl-N-methyl-tyrosyl-4-(3,4-dichlorophenyl)-piperazine;
   f. 1-[(S)—O-isoquinolinesulfonyl-N-tert-butyloxycarbonyl-N-methyl-tyrosyl]-4-(4-cyanophenyl)-piperazine];
   g. 1-[(S)—O-isoquinolinesulfonyl-N-tert-butyloxycarbonyl-N-methyl-tyrosyl]-4-(4-chlorophenyl)-piperazine];
   h. 1-[(S)—O-isoquinolinesulfonyl-N-tert-butyloxycarbonyl-N-methyl-tyrosyl]-4-(4-methoxyphenyl)-piperazine;
   i. 1-[(S)—O-isoquinolinesulfonyl-N-tert-butyloxycarbonyl-N-methyl-tyrosyl]-4-benzylpiperazine;

j. 1-[(S)—O-isoquinolinesulfonyl-N-tert-butyloxycarbonyl-N-methyl-tyrosyl]-4-(4-iodophenyl)-piperazine;
k. 1-[(S)—O-isoquinolinesulfonyl-N-tert-butyloxycarbonyl-N-methyl-tyrosyl]-4-(4-acetylphenyl)-piperazine;
l. 1-[(S)—O-isoquinolinesulfonyl-N-tert-butyloxycarbonyl-N-methyl-tyrosyl]-4-(4-fluorobenzyl)-piperazine;
m. 1-[(S)—O-isoquinolinesulfonyl-N-tert-butyloxycarbonyl-N-methyl-tyrosyl]-4-(4-fluorobenzoyl)-piperazine;
n. 1-[(S)—O-isoquinolinesulfonyl-N-tert-butyloxycarbonyl-N-methyl-tyrosyl]-4-(4-nitrobenzyl)-piperazine;
o. 1-[(S)—O-isoquinolinesulfonyl-N-tert-butyloxycarbonyl-N-methyl-tyrosyl]-4-(2-fluorophenyl)-piperazine;
p. 1-[(S)—O-isoquinolinesulfonyl-N-tert-butyloxycarbonyl-N-methyl-tyrosyl]-4-(o-tolyl)-piperazine;
q. 1-[(S)—O-isoquinolinesulfonyl-N-tert-butyloxycarbonyl-N-methyl-tyrosyl]-4-(2-methoxyphenyl)-piperazine;
r. 1-[(S)—O-isoquinolinesulfonyl-N-tert-butyloxycarbonyl-N-methyl-tyrosyl]4-(3-chlorophenyl)-piperazine;
s. 1-[(S)—O-isoquinolinesulfonyl-N-tert-butyloxycarbonyl-N-methyl-tyrosyl]-4-(3-trifluoromethylphenyl)-piperazine;
t. 1-[(S)—O-isoquinolinesulfonyl-N-tert-butyloxycarbonyl-N-methyl-tyrosyl]-4-(2,3-dimethylphenyl)-piperazine;
u. 1-[(S)—O-isoquinolinesulfonyl-N-tert-butyloxycarbonyl-N-methyl-tyrosyl-]-4-(pyridin-2-yl)-piperazine;
v. 1-[(S)—O-isoquinolinesulfonyl-N-tert-butyloxycarbonyl-N-methyl-tyrosyl]-4-(pyrimidin-2-yl)-piperazine;
w. 1-[(S)—O-isoquinolinesulfonyl-N-tert-butyloxycarbonyl-N-methyl-tyrosyl]-4-benzylpiperazine;
x. 1-[(S)—O-isoquinolinesulfonyl-N-tert-butyloxycarbony-1-tyrosyl]-4-(4-fluorophenyl)-piperidine;
y. 1-[(S)—O-isoquinolinesulfonyl-N-tert-butyloxycarbonyl-tyrosyl]-4-(o-tolyl)-piperazine;
z. 1-[(S)—O-isoquinolinesulfonyl-N-tert-butyloxycarbonyl-N-methyl-tyrosyl]-4-(4-aminophenyl)-piperazine;
aa. 1-[(S)—O-(3-pyridinesulfonyl)-N-tert-butyloxycarbonyl-tyrosyl]-4-(o-tolyl)-piperazine;
bb. 1-[(S)—O-(3-pyridinesulfonyl)-N-tert-butyloxycarbonyl-N-methyl-tyrosyl]-4-(phenyl)-piperazine;
cc. 1-[(S)—O-(3-pyridinesulfonyl)-N-tert-butyloxycarbonyl-tyrosyl]-4-(2-methylphenyl)-piperazine; and
dd. 1-[(S)—O-isoquinolinesulfonyl-N-tert-butyloxycarbonyl-tyrosyl]-4-(4-bromo-2-methylphenyl)-piperazine.

\* \* \* \* \*